United States Patent
Norris

(10) Patent No.: US 11,229,635 B2
(45) Date of Patent: Jan. 25, 2022

(54) METHOD OF TREATING FIBROSIS

(71) Applicant: BCN Biosciences L.L.C., Inglewood, CA (US)

(72) Inventor: Andrew J. Norris, Los Angeles, CA (US)

(73) Assignee: BCN Biosciences L.L.C., Inglewood, CA (US)

( * ) Notice: Subject to any disclaimer, the term of this patent is extended or adjusted under 35 U.S.C. 154(b) by 0 days.

(21) Appl. No.: 16/292,266

(22) Filed: Mar. 4, 2019

(65) Prior Publication Data

US 2019/0336493 A1 Nov. 7, 2019

Related U.S. Application Data

(63) Continuation of application No. 15/784,162, filed on Oct. 15, 2017, now abandoned.

(60) Provisional application No. 62/408,809, filed on Oct. 16, 2016.

(51) Int. Cl.
| | |
|---|---|
| *A61K 31/4709* | (2006.01) |
| *A61K 9/00* | (2006.01) |
| *A61K 47/32* | (2006.01) |
| *A61K 47/40* | (2006.01) |
| *A61K 31/635* | (2006.01) |
| *A61K 47/22* | (2006.01) |
| *A61K 47/20* | (2006.01) |
| *A61K 47/10* | (2017.01) |

(52) U.S. Cl.
CPC ........ *A61K 31/4709* (2013.01); *A61K 9/0019* (2013.01); *A61K 9/0095* (2013.01); *A61K 31/635* (2013.01); *A61K 47/10* (2013.01); *A61K 47/20* (2013.01); *A61K 47/22* (2013.01); *A61K 47/32* (2013.01); *A61K 47/40* (2013.01); *Y02A 50/30* (2018.01)

(58) Field of Classification Search
CPC ...... A61K 31/4709; A61K 9/00; A61K 47/32; A61K 47/40; A61K 31/635; A61K 47/22; A61K 47/20; A61K 47/10
See application file for complete search history.

(56) References Cited

FOREIGN PATENT DOCUMENTS

WO   WO 2014/182789   * 11/2014

OTHER PUBLICATIONS

Williams et al. in Current Drug Targets 11(11): 1386-1394 (2010) (Year: 2010).*
Oikonomou et al. in PLoS ONE 1(1): e108, pp. 1-14 (2006) (Year: 2006).*
Tumor Necrosis Factor at https://pubchem.ncbi.nlm.nih.gov/gene/7124https://pubchem.ncbi.nlm.nih.gov/gene/7124 (retrieved from the internet Oct. 1, 2020) (Year: 2020).*
Madhusudan et al. in Journal of Clinical Oncology 23(25), 5950-5959 (2005) (Year: 2005).*
Redente et al. Am J Respir Cell Mol Biol 50(4), 825-837 (2014) (Year: 2014).*
Distler et al. Arthritis & Rheumatism 58(8), 2228-2235 (2008) (Year: 2008).*
Raghu et al. Am J Respir Crit Care Med 178, 948-955 (2008) (Year: 2008).*

* cited by examiner

*Primary Examiner* — Dennis Heyer
(74) *Attorney, Agent, or Firm* — Entralta P.C.; James F. Fleming; Peter D. Weinstein

(57) ABSTRACT

The present disclosure is directed to method of treatment for treating or ameliorating various conditions pertaining such as bone marrow recovery (or blood cell production), fibrosis, inflammatory diseases, inhibition of cancer cell growth, propagation or malignancy, thrombocytopenia, wound healing, and conditions related to stem cells by the administration of BCN057, 512, or an analog thereof.

7 Claims, 23 Drawing Sheets

Figure 7A-D

Control　　　　　　　　512　　　　　　　　LTI　　　　　　　　LTI +512

Figure 11 B-C

| PANEL NME | CELLNAME | % CTRL |
|---|---|---|
| Renal Cancer | A498 | 43.82552 |
| Renal Cancer | ACHN | 45.44553 |
| Renal Cancer | UO-31 | 47.81864 |
| Renal Cancer | CAKI-1 | 50.76488 |
| Renal Cancer | 786-0 | 67.88689 |
| Renal Cancer | TK-10 | 71.02499 |
| Renal Cancer | RXF 393 | 73.4074 |
| Renal Cancer | SN12C | 76.09256 |
| Prostate Cancer | PC-3 | 46.13005 |
| Prostate Cancer | DU-145 | 71.70187 |
| Ovarian Cancer | IGROV1 | 63.3854 |
| Ovarian Cancer | NCI/ADR-RES | 68.67337 |
| Ovarian Cancer | OVCAR-4 | 69.3182 |
| Ovarian Cancer | OVCAR-5 | 70.80969 |
| Ovarian Cancer | SK-OV-3 | 78.10953 |
| Ovarian Cancer | OVCAR-8 | 78.48365 |
| Ovarian Cancer | OVCAR-3 | 89.40745 |
| Non-Small Cell Lung Cancer | HOP-92 | 20.57267 |
| Non-Small Cell Lung Cancer | EKVX | 55.85129 |
| Non-Small Cell Lung Cancer | NCI-H23 | 70.15847 |
| Non-Small Cell Lung Cancer | NCI-H322M | 74.05311 |
| Non-Small Cell Lung Cancer | NCI-H226 | 76.41622 |
| Non-Small Cell Lung Cancer | A549/ATCC | 85.16477 |
| Non-Small Cell Lung Cancer | NCI-H522 | 87.25749 |
| Non-Small Cell Lung Cancer | NCI-H460 | 88.92206 |
| Non-Small Cell Lung Cancer | HOP-62 | 90.67663 |

| PANEL NME | CELLNAME | % CTRL |
|---|---|---|
| Melanoma | UACC-62 | 45.97576 |
| Melanoma | SK-MEL-5 | 56.92246 |
| Melanoma | MALME-3M | 75.39151 |
| Melanoma | LOX IMVI | 75.80333 |
| Melanoma | SK-MEL-28 | 81.84115 |
| Melanoma | MDA-MB-435 | 86.76372 |
| Melanoma | M14 | 86.78558 |
| Melanoma | UACC-257 | 103.2457 |
| Melanoma | SK-MEL-2 | 104.812 |
| Leukemia | SR | 31.46065 |
| Leukemia | MOLT-4 | 52.74362 |
| Leukemia | RPMI-8226 | 62.29008 |
| Leukemia | CCRF-CEM | 62.29655 |
| Leukemia | HL-60(TB) | 67.46898 |
| Leukemia | K-562 | 74.28822 |
| Colon Cancer | HCT-116 | 57.49793 |
| Colon Cancer | HCT-15 | 75.8011 |
| Colon Cancer | COLO 205 | 75.9838 |
| Colon Cancer | KM12 | 77.73953 |
| Colon Cancer | HT29 | 79.92817 |
| Colon Cancer | SW-620 | 87.13555 |
| Colon Cancer | HCC-2998 | 95.55738 |
| CNS Cancer | SNB-19 | 34.58018 |
| CNS Cancer | SNB-75 | 55.95648 |
| CNS Cancer | SF-539 | 65.48454 |
| CNS Cancer | SF-268 | 71.64959 |
| CNS Cancer | SF-295 | 74.82837 |
| CNS Cancer | U251 | 75.0878 |
| Breast Cancer | T-47D | 47.06197 |
| Breast Cancer | MDA-MB-231/ATC | 49.5651 |
| Breast Cancer | HS 578T | 65.28081 |
| Breast Cancer | BT-549 | 66.12205 |
| Breast Cancer | MDA-MB-468 | 67.09269 |
| Breast Cancer | MCF7 | 74.07751 |

Figure 18 A-B
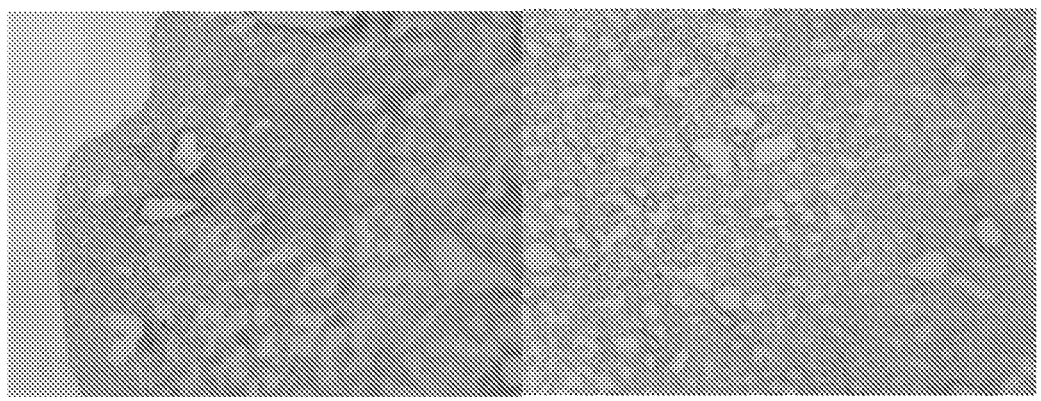
Figure 19 A-D
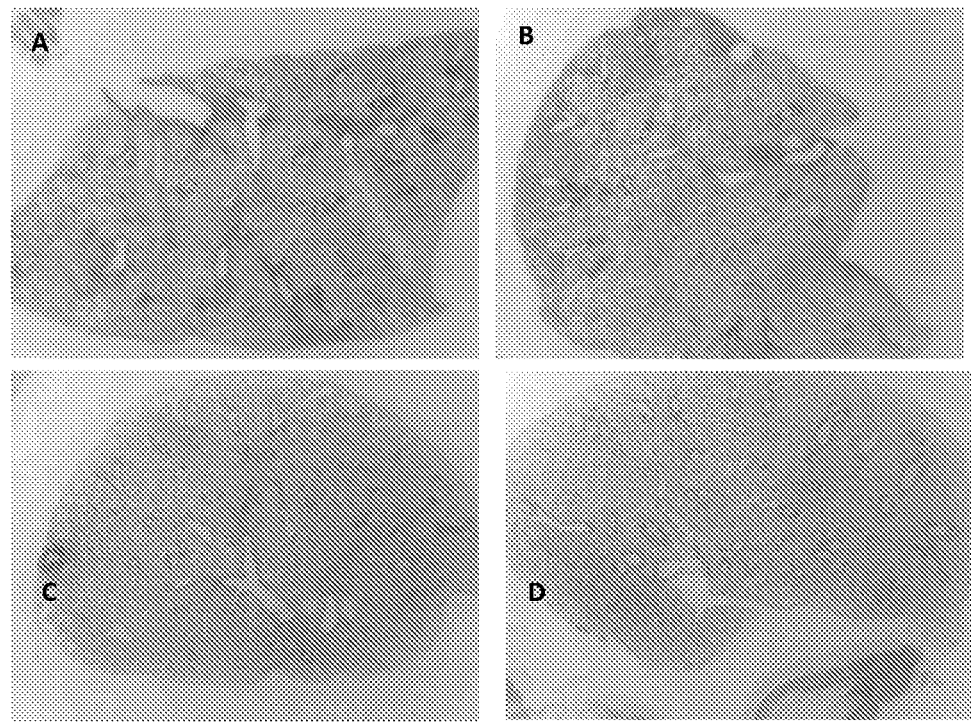

Figure 22
Species 1
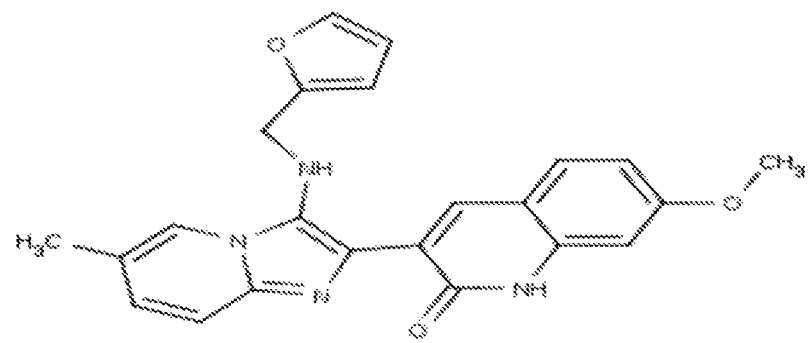
Species 2
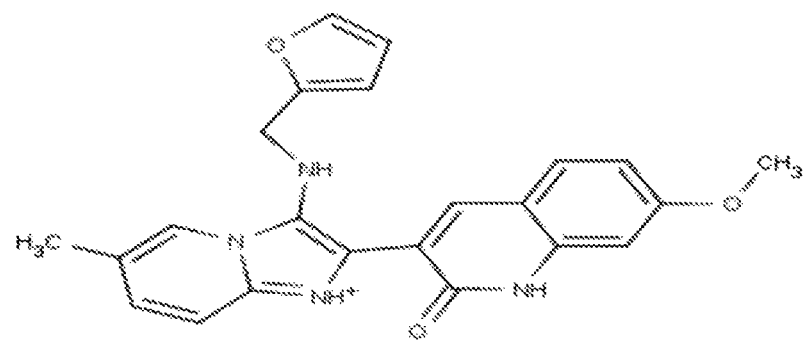
Species 3
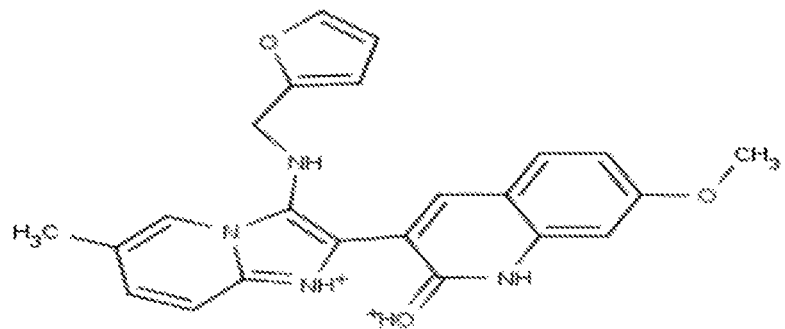

Species 4

Figure 24 A-F
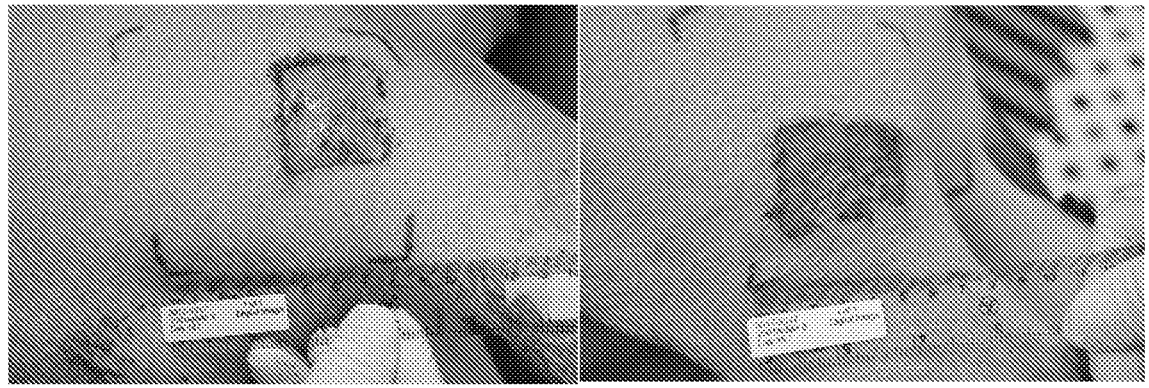
1501 Day 18 Site 3  1501 Day 18 Site 5
2501 Day 18 Site 3  2501 Day 18 Site 5
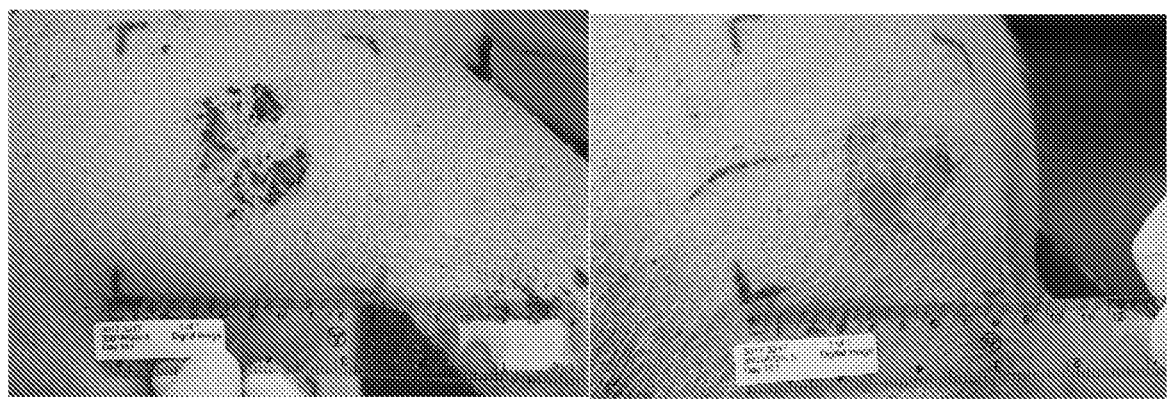
3501 Day 18 Site 3  3501 Day 18 Site 5

METHOD OF TREATING FIBROSIS

CROSS REFERENCE TO RELATED APPLICATIONS

This application claims priority to non-provisional application U.S. Pat. Ser. No. 15/784,162, filed Oct. 15, 2017; and provisional application U.S. Ser. No. 62/408,809, filed Oct. 16, 2016, herein incorporated by reference in their entirety. This application is also related to U.S. Ser. No. 13/813,923 and U.S. Ser. No. 14/889,719, herein incorporated by reference in their entirety.

BACKGROUND OF THE INVENTION

The discovery of compounds that are capable of mitigating the process of normal tissue damage from radiation during radiotherapy, accidents, or acts of war is of great importance. Most currently available treatments for radiation exposure are free radical scavengers that reduce initial radiation-induced DNA damage and work best if added just before or at the time of irradiation. Because of this, these compounds are not practical countermeasures for a radiation incident. In that case, the search for radiomitigators —agents with robust, prolonged efficacy, broad specificity, and minimal toxicity is of great importance. In addition, for applications such as radio-therapy for cancer, the compound should protect the normal tissue, but not the cancerous tissue.

The present application provides new uses for molecules that were originally identified to protect normal cells from radiation induced cell death. Fundamental to radiation exposure and injury are DNA strand breaks, resulting in genetic instability and DNA deletions which are involved in cell death, cellular dysfunction, as well as longer term consequences such as birth defects and cancer.

The compounds disclosed herein were first described in U.S. Ser. No. 13/813,923 and U.S. Ser. No. 14/889,719. The present invention provides new methods of use for these compounds, in particular the compounds BCN057 (also called YEL002) and 512, also called BCN512.

BRIEF SUMMARY OF THE INVENTION

In one aspect, the invention provides a method of increasing hematopoiesis in a subject in need thereof, the method comprising administering to the subject a therapeutically effective amount of BCN057, BCN512, or an analog thereof.

In one embodiment, the subject has leukemia, AML, ALL, bone marrow ablation, bone marrow transplant, bone marrow suppression due to radiation or chemotherapy, a platelet disorder, or clinical radiation related exposure.

In one embodiment, the platelet disorder is caused by bone marrow failure (e.g., aplastic anemia, paroxysmal nocturnal hemoglobinuria, Shwachman-Diamond syndrome), bone marrow suppression (e.g., from medication, chemotherapy, or irradiation as discussed above), chronic alcohol abuse, congenital macrothrombocytopenias (e.g., Alport syndrome, Bernard-Soulier syndrome, Fanconi anemia, platelet-type or pseudo-von Willebrand disease, Wiskott-Aldrich syndrome), infection (e.g., cytomegalovirus, Epstein-Barr virus, hepatitis C virus, HIV, mumps, parvovirus B19, rickettsia, rubella, varicella-zoster virus), myelodysplastic syndrome, neoplastic marrow infiltration, or nutritional deficiencies (vitamin B12 and folate).

In one aspect, the invention provides a method of inhibiting cancer cell growth in a subject in need thereof, the method comprising administering to the subject a therapeutically effective amount of BCN057, BCN512 or an analog thereof, wherein the cancer is selected from the group consisting of renal cancer, prostate cancer, non-small cell lung cancer, head and neck cancers, breast cancer, colon cancer, ovarian, leukemia, skin cancer such as melanoma, central nervous system cancers including pediatric brain cancers and adult brain cancers.

In one aspect, the invention provides a method of preventing late effects of clinical radiation, the method comprising administering to the subject a therapeutically effective amount of BCN057, BCN512 or an analog thereof, wherein the effects are reduction of tissue fibrosis, reduction in hormonal deficits, reduction in neurological impairment from radiation, reduction in growth retardation from radiation treatment, reduction of pulmonary, prostate, colon or kidney damage from radiation, reduction in leukemia arising from radiation treatment In one aspect, the invention provides a method of treating fibrosis in a subject in need thereof, the method comprising administering to the subject a therapeutically effective amount of BCN057, BCN512, or an analog thereof.

In one embodiment, the fibrosis is a fibrotic disease selected from the group consisting of idiopathic pulmonary fibrosis, liver fibrosis, gastrointestinal fibrosis and renal fibrosis from kidney dialysis In one embodiment, the fibrotic disease is pulmonary fibrosis, idiopathic pulmonary fibrosis, acute respiratory distress syndrome, cystic fibrosis, non-cystic fibrosis bronchiectasis, cirrhosis, liver fibrosis (caused, for example by chronic viral hepatitis B or C), endomyocardial fibrosis, old myocardial infarction, atrial fibrosis, mediastinal fibrosis (soft tissue of the mediastinum), myelofibrosis (bone marrow), retroperitoneal fibrosis, progressive massive fibrosis, nephrogenic systemic fibrosis, Crohn's disease, gastrointestinal fibrosis, keloid conditions, scleroderma/systemic sclerosis, arthofibrosis, peyronie's disease, dupuytren's contracture, oral submucous fibrosis, or adhesive capsulitis.

In one aspect, the invention provides a method of improving wound and tissue healing in a subject in need thereof, the method comprising administering to the subject a therapeutically effective amount of BCN057, BCN512 or an analog thereof.

In one embodiment, the wound is a dermal wound. In one embodiment, the wound is caused by sun, radiation or heat exposure.

In one embodiment, the analog is selected from the group consisting of Formula IB-H. In one embodiment, the compound is Formula IA. In one embodiment, the analog is selected from the group consisting of Formula IIB-H. In one embodiment, the compound is Formula IIA.

In one embodiment, the subject received radiation therapy.

In one aspect, the invention provides a pharmaceutical composition of BCN057 comprising 100 mM methanesulfonic acid/10% povidone (PVP); 100 mM MSA/2% benzyl alcohol/2% N-methylpyrrolidone (NMP).

In one embodiment, the composition comprises 30 wt % Captisol (SBE-beta-CD) and 100 mM MSA. In another embodiment, the composition further comprises 30 wt % Captisol (SBE-beta-CD) and 100 mM MSA at pH 4.0 or lower.

In one aspect, the invention provides a nanoparticle pharmaceutical composition of BCN512.

BRIEF DESCRIPTION OF THE DRAWINGS

FIG. 11A-C: (A) Cancer Cell Proliferation in the presence of BCN057 10 mM expressed as a percent of control which is considered 100%. Cancer cell proliferation rate (various lines) vs control of 10 ul BCN057 vs control which is DMSO alone. (B)-(C) Panel name, cell name and % of control.

FIG. 18A-B: Histologic examination of rodents undergoing local thoracic radiation and lung damage.

FIG. 19A-D: Histologic examination of rodents undergoing local thoracic radiation and lung damage.

FIG. 24A-F: Photos of dermal wound healing from radiation. A-B are control sites where only vehicle and no drug was used subsequent to radiation. C-D are drug treatment sites irradiated identical to the control site but with vehicle containing BCN512 at 10 mg/ml. E-F are drug treatment sites irradiated identical to the control site but with vehicle containing BCN057 at 10 mg/ml. Photographs of these subject wounds are also analyzed for Draize scoring in FIGS. 20 and 21.

DETAILED DESCRIPTION OF THE INVENTION

Introduction

Figure 1:
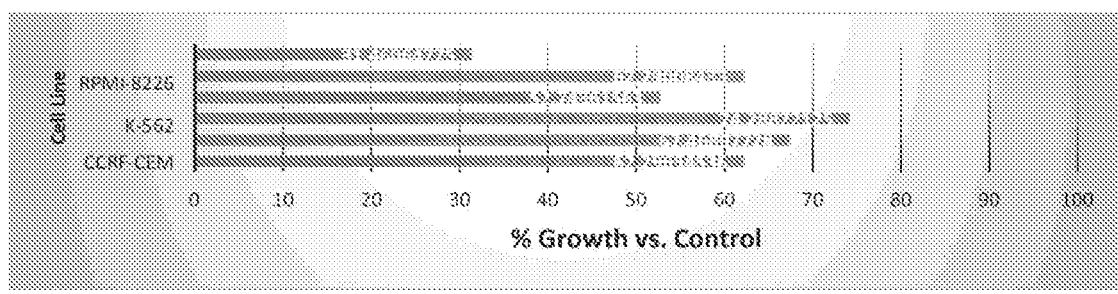
FIG. 1: Inhibition of RPMI-8226, K-562, and CCRF-CEM cell lines by BCN057.

The compounds and compositions disclosed herein, including BCN512, BCN057 and analogs thereof can be used for treating or ameliorating various conditions described herein, such as bone marrow recovery and hematopoiesis, inhibition of cancer cell growth, late effects of radiation including fibrosis, and wound healing.

Compositions

The structure of compound YEL002/BCN057 is shown below as Formula IA:

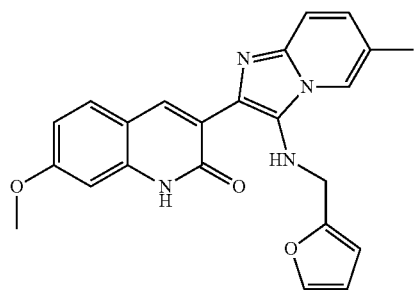 [SMILES: COc1ccc2cc(-c3nc4ccc(C)cn4c3NCc3ccco3)c(=O)[nH]c2c1]

Yel002 or BCN057 is also known as 3-(3((furan-2-ylmethyl)ammo)-6-methylimidazo[1,2-α]pyridine-2-yl)-6-methoxyquinolin-2(1H)-one.

In some embodiments, the compound is an analog of Formula IA selected from Formulae IB-IH:

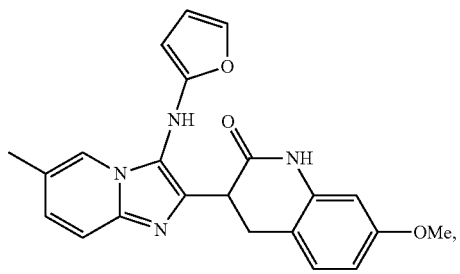

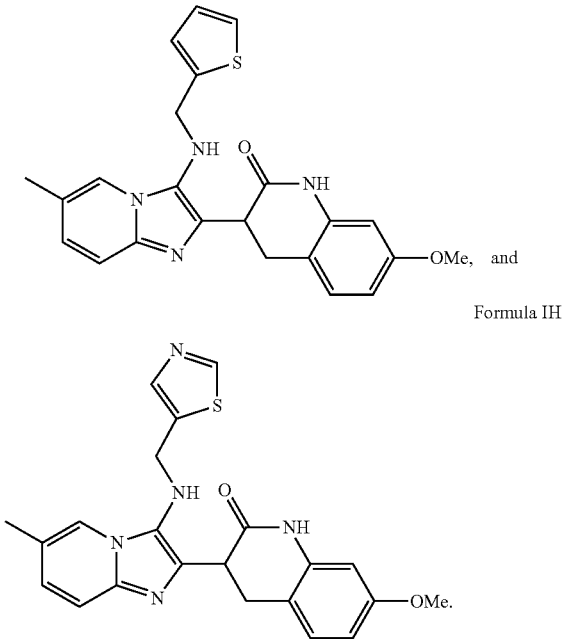

A compound of Formula IA, or an analog thereof disclosed herein can be prepared according to established methodology in the art of organic synthesis. General methods of synthesizing the compound can be found in, e.g., Stuart Warren and Paul Wyatt, Workbook for Organic Synthesis: The Disconnection Approach, second Edition, Wiley, 2010. Exemplary methods of making the compound is provided in U.S. Ser. No. 13/813,923 and U.S. Ser. No. 14/889,719, herein incorporated by reference in their entirety. The compound also includes a pharmaceutically acceptable salt thereof, a prodrug thereof, a hydrate thereof, a solvate thereof, or a polymorphic crystal thereof. The compound may be administered as a pharmaceutical composition.

The structure of compound BCN512 is shown below as Formula IIA:

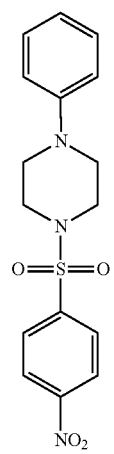

Compound 512 is also known as 1-[(4-nitrobenezene)sulfonyl]-4-phenyl piperazine. Analogs of 512 include compounds of Formula IIB:

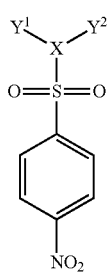

wherein:
Y$^1$ and Y$^2$ taken together with X form:

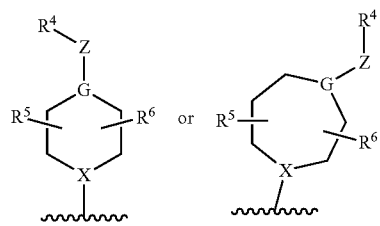

and wherein:
X is N;
G is N;
Z is absent or selected from substituted or unsubstituted alkyl, heteroalkyl, alkenyl, or alkynyl;
R$^4$ is absent or selected from substituted or unsubstituted aryl; and
R$^5$ and R$^6$ are each independently absent or lower alkyl.

In one embodiment, the analog is selected from Formulae IIC-E:

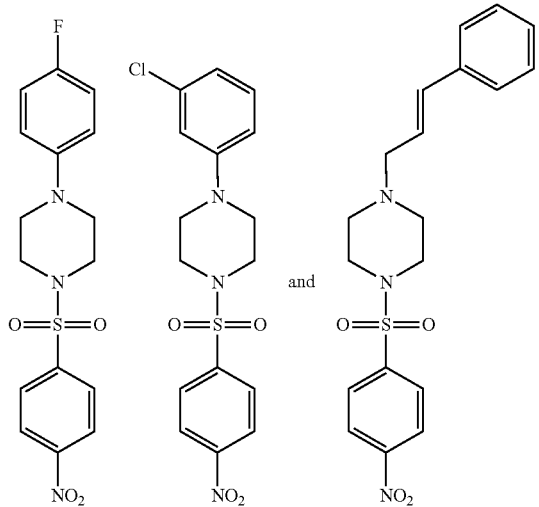

A compound of Formula IIA, or an analog thereof disclosed herein, can be prepared according to established methodology in the art of organic synthesis. General methods of synthesizing the compound can be found in, e.g., Stuart Warren and Paul Wyatt, Workbook for Organic Synthesis: The Disconnection Approach, second Edition, Wiley, 2010. Exemplary methods of making the compound is provided in U.S. Ser. No. 13/813,923 and U.S. Ser. No. 14/889,719, herein incorporated by reference in their entirety. The compound also includes a pharmaceutically acceptable salt thereof, a prodrug thereof, a hydrate thereof, a solvate thereof, or a polymorphic crystal thereof. The compound may be administered as a pharmaceutical composition.

Methods of Treatment

The compounds and compositions disclosed herein can be used for treating or ameliorating various conditions such as bone marrow recovery and hematopoiesis, inhibition of cancer cell growth, late effects of radiation including fibrosis, and wound healing.

Bone Marrow Recovery and Hematopoiesis

Some cancer treatments, including radiation therapy and chemotherapy, can affect the bone marrow so that it does not make normal numbers of blood cells. Similarly, bone marrow transplant may also reduce the production of normal numbers of blood cells. When the bone marrow doesn't work properly, blood cells are not replaced as they normally would be and blood cell counts drop. Blood cell counts usually start to drop 7-10 days or longer after treatment. The time frame depends on the type of treatment given.

The lowest level that blood cell counts reach is called the nadir. Each type of blood cell has a different nadir and nadir occurs at different times. Because RBCs live the longest, it takes them longer to reach their nadir. WBCs and platelets reach their lowest levels about 7-14 days after treatment. Symptoms of low blood cell counts are often worse at nadir. Blood cell counts may begin to recover and rise on their own, usually 2-4 weeks after radiation, chemotherapy or transplant treatment, however they may be suppressed for a significant period beyond the predicating treatment. The present methods speed bone marrow recovery.

Radiation therapy can damage tissues in the bone marrow that make blood cells. This is especially true if areas that contain large amounts of bone marrow, such as the pelvic bones, are treated with radiation. The present compositions may be administered prophylactically before the initiation of radiation therapy, concurrently with radiation therapy, in between intervals of radiation therapy, or after radiation therapy.

Bone marrow transplant may lead to suppressed bone marrow recovery. Chemotherapy can also damage tissues in the bone marrow that make blood cells. For instance, bone marrow toxicity may occur with chemotherapeutic agents such as methotrexate, doxorubicin, cyclophosphamide, ifosfamide, 5-fluorocil, 6-mercaptopurine, cytarabine, gemcitabine, fludarabine, etoposide, bleomycin, irinotecan, topotecan, vinblastine, vincristine, paclitaxel or docetaxel, cisplatin, carboplatin, oxaliplatin and iomustine. In many of these dose regimens, it is a late complication of treatment. In some cases, occurring in patients having taken a given drug for over a year, and may not be appropriately monitored. People with kidney or liver problems have a higher risk of bone marrow suppression while on chemotherapy because their bodies can't break down the chemotherapy drugs.

Thus, the present therapies may be administered to patients who are concurrently prescribed with chemotherapy or after the onset of bone marrow suppression resulting from the chemotherapy. Furthermore, the present compositions may be administered in patients with an extended period of treatment with the expectation that the present therapies will prevent, delay, or attenuate the toxicity towards bone marrow, and speed bone marrow recovery. The present methods could be applied after it is apparent that bone marrow suppression has occurred.

Advanced HIV invention may also lead to bone marrow suppression. Thus, in one embodiment, the present compositions may be administered to patients having HIV, before or after the bone marrow suppression becomes evident.

Symptoms of bone marrow suppression can vary depending on their cause and other factors. It can also vary with the type of blood cell that is affected.

Anemia (a lower number of red blood cells) causes fatigue, pale skin, lips or nail beds, increased heart rate, tiring easily with exertion, dizziness, shortness of breath, headache, irritability—more often seen in young children. Neutropenia or leukopenia (lower number of white blood cells) causes: a greater risk of infection, fever and chills if an infection is present. Thrombocytopenia (a lower number of platelets) causes easy bruising, bleeding from the nose, gums or mouth, tiny red spots on the skin, or petechiae, blood in the urine, dark or black bowel movements.

Pancytopenia refers to low levels of all 3 types of blood cells. The symptoms could include any or all of the above symptoms.

Furthermore, protection may also occur for other cells in the bone marrow such as progenitor cells, myeloid cells, stem cells, fibroblast, endo and epithelial cells, and immune cells. Accordingly, in one embodiment, the administration of the present compounds increases the production of or prevents the destruction of progenitor cells, myeloid cells, stem cells, fibroblasts, endo and epithelial cells, and immune cells.

In one embodiment, the present compounds may also be used to spur stem cell self-renewal. Hematopoietic Stem Cells (HSCs) possess the ability of both multi-potency and self-renewal. Multi-potency is the ability to differentiate into all functional blood cells. Self-renewal is the ability to give rise to HSC itself without differentiation. Since mature blood cells are predominantly short lived, HSC continuously provide more differentiated progenitors while properly maintaining the HSC pool size properly throughout life by precisely balancing self-renewal and differentiation.

In a further aspect of stem-cell self-renewal, the present compounds may be used for the stimulation of engrafted stem cells.

In certain embodiments, the therapeutic compounds disclosed herein increase production of suppressed cell populations by bone marrow by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In certain embodiments, the therapeutic compounds disclosed herein increase production of suppressed cell populations by bone marrow by, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In certain embodiments, the therapeutic compound disclosed herein increases production of suppressed cell populations by bone marrow by e.g., at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In certain embodiments, the therapeutic compound disclosed increases production of suppressed cell populations by bone marrow by, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In certain embodiments, the therapeutic compound disclosed herein reduces the duration of the symptoms of bone marrow suppression by at least 1 week, 2 weeks, 3 weeks, 4 weeks, 1 month, 2 months, 3 months, 4 months, 5 months, 6 months, 7 months, 8 months, 9 months, 10 months, 11 months, 1 year, or 2 years as compared to a patient not receiving the same treatment.

Thrombocytopenia

Thrombocytopenia is a clinically decreased number of platelets, and may be independent of bone marrow suppression. It may be caused by a decreased platelet production, increased platelet destruction, sequestration of platelets, or pseudotrombocytopenia. Multiple genetic, immune, or environmental conditions may lead to thrombocytopenia.

Decreased platelet production may be caused for example, by bone marrow failure (e.g., aplastic anemia, paroxysmal nocturnal hemoglobinuria, Shwachman-Diamond syndrome), Bone marrow suppression (e.g., from medication, chemotherapy, or irradiation as discussed above), Chronic alcohol abuse, Congenital macrothrombocytopenias (e.g., Alport syndrome, Bernard-Soulier syndrome, Fanconi anemia, platelet-type or pseudo-von Willebrand disease, Wiskott-Aldrich syndrome), Infection (e.g., cytomegalovirus, Epstein-Barr virus, hepatitis C virus, HIV, mumps, parvovirus B19, rickettsia, rubella, varicella-zoster virus), Myelodysplastic syndrome, Neoplastic marrow infiltration, or Nutritional deficiencies (vitamin B12 and folate).

Increased platelet consumption/destruction may be caused by: Alloimmune destruction (e.g., posttransfusion, neonatal, posttransplantation), Autoimmune syndromes (e.g., antiphospholipid syndrome, systemic lupus erythematosus, sarcoidosis), Disseminated intravascular coagulation/severe sepsis, Drug-induced thrombocytopenia (caused, for example, by quinidine, quinine, sulfa-containing antibiotics, interferon, anticonvulsants and gold salts), Heparin-induced thrombocytopenia, Immune thrombocytopenic purpura*, Infection (e.g., cytomegalovirus, Epstein-Barr virus, hepatitis C virus, HIV, mumps, parvovirus B19, rickettsia, rubella, varicella-zoster virus, bacteremia), Mechanical destruction (e.g., aortic valve, mechanical valve, extracorporeal bypass), Preeclampsia/HELLP syndrome, Thrombotic thrombocytopenic purpura (small blood clots suddenly form throughout the body, using up large numbers of platelets), hemolytic uremic syndrome (which causes sharp drop in platelets, destruction of red blood cells and impairment of kidney function. Sometimes it can occur in association with a bacterial *Escherichia coli* infection, such as may be acquired from eating raw or undercooked meat), idopathic thrombocytopenic purpura (ITP) (where the body's immune system mistakenly identifies platelets as a threat and forms antibodies that attack them).

Sequestration of platelets leading to thrombocytopenia may be caused by, for example, Chronic alcohol abuse, Dilutional thrombocytopenia (e.g., hemorrhage, excessive crystalloid infusion), Gestational thrombocytopenia, Hypersplenism (e.g., distributional thrombocytopenia), Liver disease (e.g., cirrhosis, fibrosis, portal hypertension), Pseudo-thrombocytopenia, Pulmonary emboli, or Pulmonary hypertension.

In addition, some causes may lead to one or more reasons for a shortage of platelets. For instance, certain infections lead to both a decreased production of platelets as well as an increased destruction of platelets. Pregnancy in general may also cause a decrease in platelet count.

The present compositions can treat thrombocytopenia by increasing the production of platelets. Thus, in one embodiment, the present compositions may be administered to treat or mitigate thrombocytopenia caused by conditions which decrease the number of platelets produced. In another aspect, the present compositions are administered to treat or mitigate thrombocytopenia caused by conditions which obtain abnormally low platelet counts by destroying platelets.

In one embodiment, the present compounds increase the platelet count by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%.

In certain embodiments, the therapeutic compound disclosed herein increases platelet count by e.g., at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In certain embodiments, the therapeutic compound disclosed herein increases platelet count by, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

Inflammatory Diseases

Compounds of the current invention may also be used for the treatment or prevention of inflammation and inflammatory diseases. Symptoms of inflammation include: decreased levels of one or more signaling agents such as IL-6 (direct signaling for regenerative activity), IL-10, Epinephrine, IL-4, IL-10, IL-13, IL-1RA, Leukotriene B4-receptor antagonism, LPS binding protein, Soluble recombinant CD-14, Soluble TNF-α receptors, Transforming growth factor-β, and/or Type II IL-1R; Increased levels of one or more signaling agents such as IL 1-beta, IL-2, IL-6 (resulting from trans-signaling), IL-8, IL-15, IFN-gamma, Leukemia inhibitory factor, Monocyte chemoattractant protein-1, Monocyte chemoattractant protein-2, Neopterin, Neutrophil elastase, Phospholipase A2, Plasminogen activator inhibitor-1, Platelet activating factor, Prostacyclins, Prostaglandins, Protein kinase, Soluble adhesion molecules, Thromboxane, TNF-α, Tyrosine kinase, Vasoactive neuropeptides, TNF-alpha, GCSF, GMCSF, and/or EGF; swelling, cellular infiltrate (e.g., with lymphocytes and macrophages), and increased cellular matrix.

Examples of inflammatory conditions, which may be treated or prevented by the administration of a compound of the invention include, but are not limited to, inflammation of the lungs, joints, connective tissue, eyes, nose, bowel, kidney, liver, skin, central nervous system, vascular system and heart. In certain embodiments, inflammatory conditions which may be treated by the current invention include inflammation due to the infiltration of leukocytes or other immune effector cells into affected tissue. Other relevant examples of inflammatory conditions which may be treated by the present invention include inflammation caused by infectious agents, including, but not limited to, viruses, bacteria fungi and parasites.

Inflammatory lung conditions include, but are not limited to, asthma, adult respiratory distress syndrome, bronchitis, pulmonary inflammation, pulmonary fibrosis, and cystic fibrosis (which may additionally or alternatively involve the gastro-intestinal tract or other tissue(s)). Inflammatory joint conditions include rheumatoid arthritis, rheumatoid spondylitis, juvenile rheumatoid arthritis, osteoarthritis, gouty arthritis and other arthritic conditions. Eye diseases with an inflammatory component include, but are not limited to, uveitis (including iritis), conjunctivitis, scleritis, keratoconjunctivitis sicca, and retinal diseases, including, but not limited to, diabetic retinopathy, retinopathy of prematurity, retinitis pigmentosa, and dry and wet age-related macular degeneration. Inflammatory bowel conditions include chronic inflammation of all or part of the digestive tract, Crohn's disease (including general inflammation of the digestive tract, inflammation of the bowel wall, inflammation of the ileum, inflammation of the colon, and the sequelae of Chrohn's disease, such as fibrostenosis, fistula and obstructions), ulcerative colitis (including ulcerative proctitis, proctosigmoiditis, left-sided colitis, pancolitis, and acute severe ulcerative colitis), and distal proctitis. In one aspect, the inflammatory bowel disease also includes collagenous colitis, lymphocytic colitis. In one embodiment, the inflammatory bowel conditions are Crohn's disease, ulcerative colitis, and distal proctitis. General symptoms of these conditions include: diarrhea, abdominal pain, cramping, fatigue, anal pain, blood in the stool, reduced appetite, and unintended weight loss.

Inflammatory skin diseases include, but are not limited to, conditions associated with cell proliferation, such as psoriasis, eczema and dermatitis, (e.g., eczematous dermatitides, topic and seborrheic dermatitis, allergic or irritant contact dermatitis, eczema craquelee, photoallergic dermatitis, phototoxic dermatitis, phytophotodermatitis, radiation dermatitis, and stasis dermatitis). Other inflammatory skin diseases include, but are not limited to, scleroderma, ulcers and erosions resulting from trauma, burns, bullous disorders, or ischemia of the skin or mucous membranes, several forms of ichthyoses, epidermolysis bullosae, hypertrophic scars, keloids, cutaneous changes of intrinsic aging, photoaging, frictional blistering caused by mechanical shearing of the skin and cutaneous atrophy resulting from the topical use of corticosteroids. Additional inflammatory skin conditions include inflammation of mucous membranes, such as cheilitis, chapped lips, nasal irritation, mucositis and vulvovaginitis.

Inflammatory disorders of the endocrine system include, but are not limited to, autoimmune thyroiditis (Hashimoto's disease), Type I diabetes, and acute and chronic inflammation of the adrenal cortex. Inflammatory conditions of the cardiovascular system include, but are not limited to, coronary infarct damage, peripheral vascular disease, myocarditis, vasculitis, revascularization of stenosis, artherosclerosis, and vascular disease associated with Type II diabetes.

Inflammatory condition of the kidney include, but are not limited to, glomerulonephritis, interstitial nephritis, lupus nephritis, nephritis secondary to Wegener's disease, acute renal failure secondary to acute nephritis, Goodpasture's syndrome, post-obstructive syndrome, tubular ischemia, irritable bowel disorder, or inflammation induced colon malignancies.

Inflammatory conditions of the liver include, but are not limited to, hepatitis (arising from viral infection, autoimmune responses, drug treatments, toxins, environmental agents, or as a secondary consequence of a primary disorder), biliary atresia, primary biliary cirrhosis and primary sclerosing cholangitis.

Inflammatory conditions of the central nervous system include, but are not limited to, multiple sclerosis and neurodegenerative diseases such as Alzheimer's disease, Parkinson's disease, or dementia associated with HIV infection.

Other inflammatory conditions include periodontal disease, tissue necrosis in chronic inflammation, endotoxin shock, smooth muscle proliferation disorders, graft versus host disease, tissue damage following ischemia reperfusion injury, idiopathic pulmonary fibrosis, and tissue rejection following transplant surgery.

In one embodiment, the condition is idiopathic pulmonary fibrosis. Symptoms of idiopathic pulmonary fibrosis include a dry, non-productive cough on exertion; progressive exertional dyspnea; dry, inspiratory bibasilar crackles on auscultation; clubbing of the digits; and abnormal pulmonary function tests with evidence of restriction and impaired gas exchange.

The present invention further provides a method of treating or preventing inflammation associated with post-surgical wound healing in a patient comprising administering to said patient a compound of the invention.

It should be noted that compounds of the current invention may be used to treat or prevent any disease which has an inflammatory component, such as those diseases cited above. Further, the inflammatory conditions cited above are meant to be exemplary rather than exhaustive.

Those skilled in the art would recognize that additional inflammatory conditions (e.g., systemic or local immune imbalance or dysfunction due to an injury, an insult, infection, inherited disorder, or an environmental intoxicant or perturbant to the subject's physiology) may be treated or prevented by compounds of the current invention. Thus, the methods of the current invention may be used to treat or prevent any disease which has an inflammatory component, including, but not limited to, those diseases cited above.

In certain embodiments, the therapeutic compound disclosed herein decreases one or more symptoms of inflammation by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In certain embodiments, the therapeutic compound disclosed herein decreases one or more symptoms of inflammation by, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In certain embodiments, the therapeutic compound disclosed herein decreases one or more symptoms of inflammation by e.g., at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In certain embodiments, the therapeutic compound disclosed herein decreases one or more symptoms of inflammation by, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In certain embodiments, the therapeutic compound disclosed herein reduces the duration of one or more symptoms of inflammation for at least 1 week, 2 weeks, 3 weeks, 4 weeks, 1 month, 2 months, 3 months, 4 months, 5 months, 6 months, 7 months, 8 months, 9 months, 10 months, 11 months, 1 year, 2 years, 3 years, 5 years, 6 years, 7 years, 8 years, 9 years, or 10 years as compared to a patient not receiving the same treatment.

Fibrosis

The present compositions prevent the generation of fibrosis while simultaneously supporting wound healing. Recruitment of inflammatory cells and the subsequent laying down of extracellular matrix during wound repair is a normal and healthy response to tissue damage as cells in the vicinity of the wound become activated and migrate to fill the breach. However, the general end point of repair is excessive and poorly ordered matrix deposition and fibrosis, which affects normal-tissue architecture and ultimately can disable proper functioning of tissues. This occurs on a macro scale as well as micro-scale. However, there is also fibrosis that is independent of the inflammatory response, for example, radiation induced fibrosis.

Wherever adult tissue is damaged, there is a massive influx of leukocytes in order to prevent infection. However, along with their involvement in innate immunity, leukocytes also release factors that influence the behavior of other cells around them. It is known that inflammatory cells secrete factors that stimulate fibroblast growth and many studies have indicated that inflammation may be beneficial to the repair process. For example, an early study of the messenger RNAs expressed by activated macrophages at a wound site indicated transforming growth factor (TGF), platelet-derived growth factor (PDGF), and TGF as growth factors that are delivered by recruited macrophages, and each one of these growth factors has been shown in some way or other to be beneficial in wound healing. Many more such factors are released by one or more of the infiltrating leukocytic lineages and almost all of these factors will possibly have some positive effect on some aspect of repair, be it keratinocyte motility, fibroblast proliferation or contraction, or the wound angiogenic response. However, leukocytes can also be bad for repair and may actually promote fibrosis.

Every organ of the body can mount a repair response that generally results in a fibrotic lesion. Lung fibrosis as a result of chronic obstructive pulmonary disease and liver fibrosis because of hepatitis infection are just two examples.

Thus, the present compositions may be administered to treat, ameliorate, delay the onset of, or decrease the extent of fibrosis in conditions such as pulmonary fibrosis, idiopathic pulmonary fibrosis, acute respiratory distress syndrome, cystic fibrosis, non-cystic fibrosis bronchiectasis, cirrhosis, liver fibrosis (caused, for example by chronic viral hepatitis B or C), endomyocardial fibrosis, old myocardial infarction, atrial fibrosis, mediastinal fibrosis (soft tissue of the mediastinum), myelofibrosis (bone marrow), retroperitoneal fibrosis, progressive massive fibrosis, nephrogenic systemic fibrosis, Crohn's disease, gastrointestinal fibrosis, keloid conditions, scleroderma/systemic sclerosis, arthofibrosis, peyronie' s disease, dupuytren's contracture, oral submucous fibrosis, or adhesive capsulitis. In a certain embodiment, the present compounds are administered before, concurrent with, or after kidney dialysis, as kidney dialysis is known to cause kidney fibrosis.

Symptoms of fibrosis include but are not limited to shortness of breath, a dry cough, a persistent cough with thick spit and mucous, wheezing, fatigue, unexplained weight loss, aching muscles and joints, breathlessness, repeated lung infections, inflamed nasal passages, greasy stinky stools, poor weight gain and growth, intestinal blockage, severe constipation, fibroids in the liver, inability to open mouth or limited range, persistent diarrhea, rectal bleeding, urgent need to move bowels, abdominal cramp and pain, sensation of incomplete evacuation of bowel, constipation, fever and fatigue, mouth sores, perineal disease, stiffness of joint, inability to straighten or flex joint, itchy skin, growing scar tissue on skin, lumpy or ridged scar tissue, hardening or skin or epithelial tissues, acid reflux, numbness, decreased or lack of urine output, or hemorrhaging from death of intestinal tissue.

In certain embodiments, a therapeutic compound disclosed herein reduces one or more symptoms of fibrosis by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein reduces the area affected by fibrosis by, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In certain embodiments, the therapeutic compound disclosed herein has a decreased area affected by fibrosis by e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In certain embodiments, the therapeutic compound disclosed herein has a decreased area affected by fibrosis by, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In certain embodiments, the therapeutic compound disclosed herein delays the onset of symptoms of fibrosis by at least 1 week, 2 weeks, 3 weeks, 4 weeks, 1 month, 2 months, 3 months, 4 months, 5 months, 6 months, 7 months, 8 months, 9 months, 10 months, 11 months, 1 year, 2 years, 3 years, 5 years, 6 years, 7 years, 8 years, 9 years, or 10 years as compared to a patient not receiving the same treatment.

In certain embodiments, a therapeutic compound disclosed herein reduces the size of a wound by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein reduces the size of a wound by, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Wound Healing

Furthermore, in certain embodiments the therapeutic compound or compositions disclosed herein are administered to treat, ameliorate, delay the onset of, or decrease the extent of an acute wound (such as a burn, sun exposure or radiation), e.g., dermal wounds and internal wounds, and chronic wounds such as a diabetic foot ulcer, venous leg ulcer, ulcerous tissue caused by repeated trauma to the body, or impaired wound healing due to age. Thus, the compounds disclosed herein may treat a burn, a diabetic foot ulcer, a venous leg ulcer, ulcerous tissue caused by repeated trauma to the body, or a chronic wound due to age.

In certain embodiments, the therapeutic compound disclosed herein has a decreased wound depth or area by e.g., at least at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In certain embodiments, the therapeutic compound disclosed herein has a decreased depth or area by, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20° A to about 80%, about 30% to about 80%, about 40% to about 80%, about 50% to about 80%, or about 60% to about 80%, about 10% to about 70%, about 20% to about 70%, about 30° A to about 70%, about 40% to about 70%, or about 50% to about 70% as compared to a patient not receiving the same treatment.

In certain embodiments, the therapeutic compound or compositions disclosed herein speeds the healing of the wound by at least 1 week, 2 weeks, 3 weeks, 4 weeks, 1 month, 2 months, 3 months, 4 months, 5 months, 6 months, 7 months, 8 months, 9 months, 10 months, 11 months, 1 year, 2 years, 3 years, 5 years, 6 years, 7 years, 8 years, 9 years, or 10 years as compared to a patient not receiving the same treatment.

Cancer

The present methods may also be for the treatment of cancer by the inhibition of cancer cell growth, propagation, or metastases. The actual symptoms associated with cancer are well known and can be determined by a person of ordinary skill in the art by taking into account one or more factors, including, without limitation, the location of the cancer, the cause of the cancer, the severity of the cancer, and/or the tissue or organ affected by the cancer. Those of skill in the art will know the appropriate symptoms or indicators associated with a specific type of cancer and will know how to determine if an individual is a candidate for treatment as disclosed herein.

Exemplary forms of cancer which may be treated by the subject methods include, but are not limited to, leukemia, non-Hodgkin's lymphoma, prostate cancer, bladder cancer, lung cancer (including either small cell or non-small cell cancer), colon cancer, kidney cancer, liver cancer, breast cancer, cervical cancer, endometrial or other uterine cancer, ovarian cancer, skin cancer (e.g., melanoma), testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer. In one particular embodiment, the present methods include treatment of leukemias such as acute myeloid leukemia or acute lymphocytic leukemia. In another embodiment, the present methods include treatment of breast cancer, lung carcinoma, prostate cancer, central nervous system cancer, melanoma, ovarian cancer, renal, and/or colon cancer. In one particular aspect, the present methods may treat the sequelae pediatric brain cancer, such as the effects of whole-brain irradiation, and the prevention of cognitive deficits due to brain tissue damage resulting from radiation. For instance, the present compositions may be administered prior to, during, or after brain irradiation to maintain cognitive function by protecting normal brain tissue.

In certain embodiments, a therapeutic compound or compositions disclosed herein reduces the size of a tumor by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound or compositions disclosed herein reduces the size of a tumor from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In certain embodiments, a cancer therapeutic disclosed herein is capable of reducing the number of cancer cells in an individual suffering from a cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In other aspects of this embodiment, a cancer therapeutic is capable of reducing the number of cancer cells in an individual suffering from a cancer by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In certain embodiments, a therapeutically effective amount of a cancer therapeutic disclosed herein reduces the cancer cell population and/or tumor cell size in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a cancer therapeutic disclosed herein reduces or maintains a cancer cell population and/or tumor cell size in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a cancer therapeutic disclosed herein reduces or maintains a cancer cell population and/or tumor cell size in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30° A to about 50%.

Dosage and Pharmaceutical Compositions

The present methods may prevent a disease or condition or one or more symptoms of a disease or condition. As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

The compositions and methods of the present invention may be utilized to treat an individual in need thereof. In certain embodiments, the individual is a mammal such as a human, or a non-human mammal. When administered to an animal, such as a human, the composition or the compound is preferably administered or used as a pharmaceutical composition comprising, for example, a compound of the invention and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch.

A pharmaceutical composition disclosed herein may comprise a therapeutic compound in an amount sufficient to allow customary administration to an individual. In certain embodiments, a pharmaceutical composition disclosed herein may comprise, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In certain embodiments, a pharmaceutical composition disclosed herein may comprise, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a pharmaceutical composition disclosed herein may comprise in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still certain embodiments, a pharmaceutical composition disclosed herein may comprise in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

A pharmaceutical composition disclosed herein may comprise a solvent, emulsion or other diluent in an amount sufficient to dissolve a therapeutic compound disclosed herein. In certain embodiments, a pharmaceutical composition disclosed herein may comprise a solvent, emulsion or a diluent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In certain embodiments, a pharmaceutical composition disclosed herein may comprise a solvent, emulsion or other diluent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2%

(v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

The final concentration of a therapeutic compound disclosed herein in a pharmaceutical composition disclosed herein may be of any suitable concentration. In certain embodiments, the final concentration of a therapeutic compound in a pharmaceutical composition may be a therapeutically effective amount. In certain embodiments, the final concentration of a therapeutic compound in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In certain embodiments, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In certain embodiments, the final concentration of a therapeutic compound in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

In certain embodiments, a therapeutically effective amount of a therapeutic compound disclosed herein generally is in the range of about 0.001 mg/kg/day to about 100 mg/kg/day. In certain embodiments, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In certain embodiments, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, about 0.001 mg/kg/day to about 100 mg/kg/day, about 0.001 mg/kg/day to about 150 mg/kg/day, about 0.001 mg/kg/day to about 200 mg/kg/day, about 0.001 mg/kg/day to about 250 mg/kg/day, about 0.001 mg/kg/day to about 300 mg/kg/day, about 0.001 mg/kg/day to about 350 mg/kg/day, about 0.001 mg/kg/day to about 400 mg/kg/day, about 0.001 mg/kg/day to about 450 mg/kg/day, about 0.001 mg/kg/day to about 500 mg/kg/day, about 0.001 mg/kg/day to about 550 mg/kg/day, about 0.001 mg/kg/day to about 600 mg/kg/day, about 0.001 mg/kg/day to about 650 mg/kg/day, about 0.001 mg/kg/day to about 700 mg/kg/day, about 0.001 mg/kg/day to about 750 mg/kg/day, or about 0.001 mg/kg/day to about 800 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, about 0.01 mg/kg/day to about 100 mg/kg/day, about 0.01 mg/kg/day to about 150 mg/kg/day, about 0.01 mg/kg/day to about 200 mg/kg/day, about 0.01 mg/kg/day to about 250 mg/kg/day, about 0.01 mg/kg/day to about 300 mg/kg/day, about 0.01 mg/kg/day to about 350 mg/kg/day, about 0.01 mg/kg/day to about 400 mg/kg/day, about 0.01 mg/kg/day to about 450 mg/kg/day, about 0.01 mg/kg/day to about 500 mg/kg/day, about 0.01 mg/kg/day to about 550 mg/kg/day, about 0.01 mg/kg/day to about 600 mg/kg/day, about 0.01 mg/kg/day to about 650 mg/kg/day, about 0.01 mg/kg/day to about 700 mg/kg/day, about 0.01 mg/kg/day to about 750 mg/kg/day, or about 0.01 mg/kg/day to about 800 mg/kg/day. In certain embodiments, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, about 0.1 mg/kg/day to about 100 mg/kg/day, about 0.1 mg/kg/day to about 150 mg/kg/day, about 0.1 mg/kg/day to about 200 mg/kg/day, about 0.1 mg/kg/day to about 250 mg/kg/day, about 0.1 mg/kg/day to about 300 mg/kg/day, about 0.1 mg/kg/day to about 350 mg/kg/day, about 0.1 mg/kg/day to about 400 mg/kg/day, about 0.1 mg/kg/day to about 450 mg/kg/day, about 0.1 mg/kg/day to about 500 mg/kg/day, about 0.1 mg/kg/day to about 550 mg/kg/day, about 0.1 mg/kg/day to about 600 mg/kg/day, about 0.1 mg/kg/day to about 650 mg/kg/day, about 0.1 mg/kg/day to about 700 mg/kg/day, about 0.1 mg/kg/day to about 750 mg/kg/day, or about 0.1 mg/kg/day to about 800 mg/kg/day. In certain embodiments, an effective amount of a therapeutic compound disclosed herein may be in the range of, e.g., about 10 mg/kg/day to about 15 mg/kg/day, about 10 mg/kg/day to about 20 mg/kg/day, about 10 mg/kg/day to about 25 mg/kg/day, about 10 mg/kg/day to about 30 mg/kg/day, about 10 mg/kg/day to about 35 mg/kg/day, about 10 mg/kg/day to about 40 mg/kg/day, about 10 mg/kg/day to about 45 mg/kg/day, about 10 mg/kg/day to about 50 mg/kg/day, about 10 mg/kg/day to about 75 mg/kg/day, about 10 mg/kg/day to about 100 mg/kg/day, about 10 mg/kg/day to about 150 mg/kg/day, about 10 mg/kg/day to about 200 mg/kg/day, about 10 mg/kg/day to about 250 mg/kg/day, about 10 mg/kg/day to about 300 mg/kg/day, about 10 mg/kg/day to about 350 mg/kg/day, about 10 mg/kg/day to about 400 mg/kg/day, about 10 mg/kg/day to about 450 mg/kg/day, about 10 mg/kg/day to about 500 mg/kg/day, about 10 mg/kg/day to about 550 mg/kg/day, about 10 mg/kg/day to about 600 mg/kg/day, about 10 mg/kg/day to about 650 mg/kg/day, about 10 mg/kg/day to about 700 mg/kg/day, about 10 mg/kg/day to about 750 mg/kg/day, or about 10 mg/kg/day to about 800 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In certain embodiments, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In liquid and semi-solid formulations, a concentration of a therapeutic compound disclosed herein typically may be between about 50 mg/mL to about 1,000 mg/mL. In certain embodiments, a therapeutically effective amount of a therapeutic disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

As used herein, "mitigating" means reducing one or more negative symptoms of a condition, relative to a cell, organ, tissue, or organism displaying the symptom or condition for the same amount of time, but untreated.

In some embodiments, contacting the cell, organ, tissue, or organism the present compounds may comprise administering a therapeutically effective amount of the compound to a subject. As used herein, a "therapeutically effective amount" is an amount sufficient to mitigate the negative symptom or condition.

The subject may be a human, rat, mouse, cat, dog, horse, sheep, cow, monkey, avian, or amphibian. In another embodiment, the cell is in vivo or in vitro. Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

The cell, organ, tissue, or organism may be contacted with a compound described herein before, during, or after evidencing symptoms of the condition or disease, or before the predicate event leading to an expected condition or disease. In some embodiments, the compound may be administered prophylactically, e.g., where radiation-induced thrombocytopenia is expected, before the predicate event of exposure to ionizing radiation, for example, prior to cancer radiation therapy or X-ray, or prior to development of fibrosis in advanced HIV. In some embodiments, the compound may be administered during the predicate event, or upon repeated exposure to the predicate event. In some embodiments, the compound may be administered after the predicate event, such as after exposure to ionizing radiation, or after the initiation of exposure to radiation.

When administering to an organism, the compound may be administered by any suitable means. In some embodiments, the compounds or formulations are administered orally. In some embodiments, the compounds or formulations are administered by injection, e.g. subcutaneous, parenteral, or intravenous, injections.

In some embodiments, the compound may be administered in combination with other potential mitigators or with other toxic agents such as the chemotherapeutic drugs discussed above. In a particular embodiment, the composition may be administered with growth factors, NSAIDs, chemotherapeutics, anti-inflammatories, antibiotics, Metformin (Glucophage, Glumetza, others), Sulfonylureas, Meglitinides, Thiazolidinediones, DPP-4 inhibitors, GLP-1 receptor agonists, SGLT2 inhibitors, and/or Insulin therapy, for the treatment of the above conditions. In one aspect, the growth factor can be G-CSF (aka filgrastim, NEUPOGEN®) or erythropoietin (aka EPOGEN®)

In other embodiments, the compositions may comprise an effective amount of a modulator and/or other pharmaceutically active agent in a physiologically-acceptable carrier. The carrier may take a wide variety of forms depending on the form of preparation desired for a particular route of administration. Suitable carriers and their formulation are described, for example, in Remington's Pharmaceutical Sciences by E. W. Martin.

In some embodiments, the compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) or oral administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

In some embodiments, the compositions may be in a form suitable for administration by sterile injection. In one example, to prepare such a composition, the compositions(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). For parenteral formulations, the carrier will usually comprise sterile water, though other ingredients, for example, ingredients that aid solubility or for preservation, may be included. Injectable solutions may also be prepared in which case appropriate stabilizing agents may be employed. In one embodiment, the formulation includes at least one or more of methanesulfonic acid, povidone, benzyl alcohol, n-Methyl pyrrolidone, ethaonol, Poloxamer 188, lactic acid, Captisol (SBE-beta-CD), or Vitamin E, such as TPGS (d-alpha tocopheryl polyethylene glycol 1000 succinate).

Formulations suitable for parenteral administration usually comprise a sterile aqueous preparation of the compound, which may be isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or localized delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

In some embodiments, the compositions may be in a form suitable for oral administration. In compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. If desired, tablets may be sugar coated or enteric coated by standard techniques.

Compositions suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught. Formulations for oral use include tablets containing active ingredient(s) in a mixture with pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

A syrup may be made by adding the compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

In some embodiments, the composition may be in a form of nasal or other mucosal spray formulations (e.g. inhalable forms). These formulations can include purified aqueous solutions of the active compounds with preservative agents and isotonic agents. Such formulations can be adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

In some embodiments, the composition may be in a form suitable for rectal administration. These formulations may be presented as a suppository with a suitable carrier such as cocoa butter, hydrogenated fats, or hydrogenated fatty carboxylic acids.

In some embodiments, the composition may be in a form suitable for transdermal administration. These formulations may be prepared, for example, by incorporating the active compound in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, compositions of the invention may further include one or more accessory ingredient(s) selected from encapsulants, diluents, buffers, flavoring agents, binders, disintegrants, surface active agents, thickeners, lubricants, preservatives (including antioxidants), and the like.

In some embodiments, compositions may be formulated for immediate release, sustained release, delayed-onset release or any other release profile known to one skilled in the art.

In some embodiments, the pharmaceutical composition may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that target the site of a pathology. For some applications, controlled release formulations obviate the need for frequent dosing to sustain activity at a medically advantageous level.

In a certain embodiment or a particular formulation BCN057 was solubalized in aqueous solution at physiologically compatible pHs using 100 mM methanesulfonic acid (MSA)/10% povidone (PVP); 100 mM MSA/2% benzyl alcohol/2% N-methylpyrrolidone (NMP); and, 100 mM MSA/10% ethanol/1% Poloxamer 188. In a further aspect 100 mM lactic acid was added and also improved solubility for these mixtures. In yet another embodiment, a formulation comprising BCN057 and 30 wt % Captisol (SBE-beta-CD) and 100 mM MSA yielded excellent solubility at up to pH 4.1 or higher.

In another embodiment formulation for intravenous, subcutaneous and oral delivery of therapeutic levels of BCN057 were developed comprising 30 wt % Captisol (SBE-beta-CD) and 100 mM MSA at pH 4.1 or higher (adjusted with 1.0 N NaOH).

In one embodiment for 512, formulations containing DMA (dimethylacetimide) or DMSO or Polyvinylepyrolidone are used. Suspensions (micron or nano diameter particle sizes) are useful for the drug since it wants to self-associate and crash out otherwise.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound is formulated with appropriate excipients into a pharmaceutical composition that, upon administration, releases the compound in a controlled manner. Examples include single or multiple unit tablet or capsule compositions, oil solutions, suspensions, emulsions, microcapsules, microspheres, molecular complexes, nanoparticles, patches, and liposomes.

In some embodiments, the composition may comprise a "vectorized" form, such as by encapsulation of the compound in a liposome or other encapsulate medium, or by fixation of the compound, e.g., by covalent bonding, chelation, or associative coordination, on a suitable biomolecule, such as those selected from proteins, lipoproteins, glycoproteins, and polysaccharides.

In some embodiments, the composition can be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents. Alternatively, the compound may be incorporated in biocompatible carriers, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

In all embodiments, the compound or other active compounds may be present as pharmaceutically acceptable salts or other derivatives, such as ether derivatives, ester derivatives, acid derivatives, and aqueous solubility altering derivatives of the active compound. Derivatives include all individual enantiomers, diastereomers, racemates, and other isomers of the compounds. Derivatives also include all polymorphs and solvates, such as hydrates and those formed with organic solvents, of the compounds. Such isomers, polymorphs, and solvates may be prepared by methods known in the art, such as by regiospecific and/or enantioselective synthesis and resolution.

The ability to prepare salts depends on the acidity or basicity of the compounds. Suitable salts of the compounds include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic, cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methyl sulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compounds.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Unless the context clearly indicates otherwise, compositions of all embodiments can comprise various pharmaceutically acceptable salts, or other derivatives described above.

The formulation and preparation of such compositions are well known to those skilled in the art of pharmaceutical formulation. Formulations can be found in Remington: The Science and Practice of Pharmacy.

The amount of the compound employed in the present invention to be used varies according to the condition, the patient/subject, and the extent of the condition.

The contents of all cited references (including literature references, issued patents, published patent applications) as cited throughout this application are hereby expressly incorporated by reference. The invention and the manner and process of making and using it, are described in such full, clear, concise and exact terms as to enable any person skilled in the art to which it pertains, to make and use the same.

The term "unit dosage form" or "unit" as used herein refers to physically discrete units suitable as unitary dosages for human and animal subjects, each unit containing a predetermined quantity of the compound calculated in an amount sufficient to produce the desired effect in association with a pharmaceutically acceptable, diluent, carrier or vehicle. The specifications for the novel unit dosage forms of the present invention depend on the particular compound employed and the effect to be achieved, and the pharmacodynamics associated with each compound in the subject.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

Dosing can be single dosage or cumulative (serial dosing), and can be readily determined by one skilled in the art. For instance, treatment may comprise a one-time administration of an effective dose of a pharmaceutical composition disclosed herein. Alternatively, treatment may comprise multiple administrations of an effective dose of a pharmaceutical composition carried out over a range of time periods, such as, e.g., once daily, twice daily, thrice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

In certain embodiments, the period of administration of a therapeutic compound is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In certain embodiments, a treatment regimen may comprise a period during which administration is stopped for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

The patient receiving this treatment is any animal in need, including primates, in particular humans, and other mammals such as equines, cattle, swine and sheep; and poultry and pets in general.

In other embodiments, the compounds described herein may be provided with the one or more additional therapeutic agents in a kit, e.g., as separate pharmaceutical formulations capable of being used together in a conjoint therapy as discussed herein, either together in a single container or in separate containers. In certain such embodiments, the kit may further include instructions for the conjoint administration of the pharmaceutical formulations, e.g., for treating or preventing any of the conditions discussed above.

Such combination products may employ compounds of this invention, or pharmaceutically acceptable salts thereof, within the dosage range described hereinbefore and the other pharmaceutically-active agent within its approved dosage range.

The invention now being generally described, it will be more readily understood by reference to the following examples which are included merely for purposes of illustration of certain aspects and embodiments of the present invention, and are not intended to limit the invention.

EXAMPLES

Example 1: Cancer Cell Growth Inhibition

Figure 2:
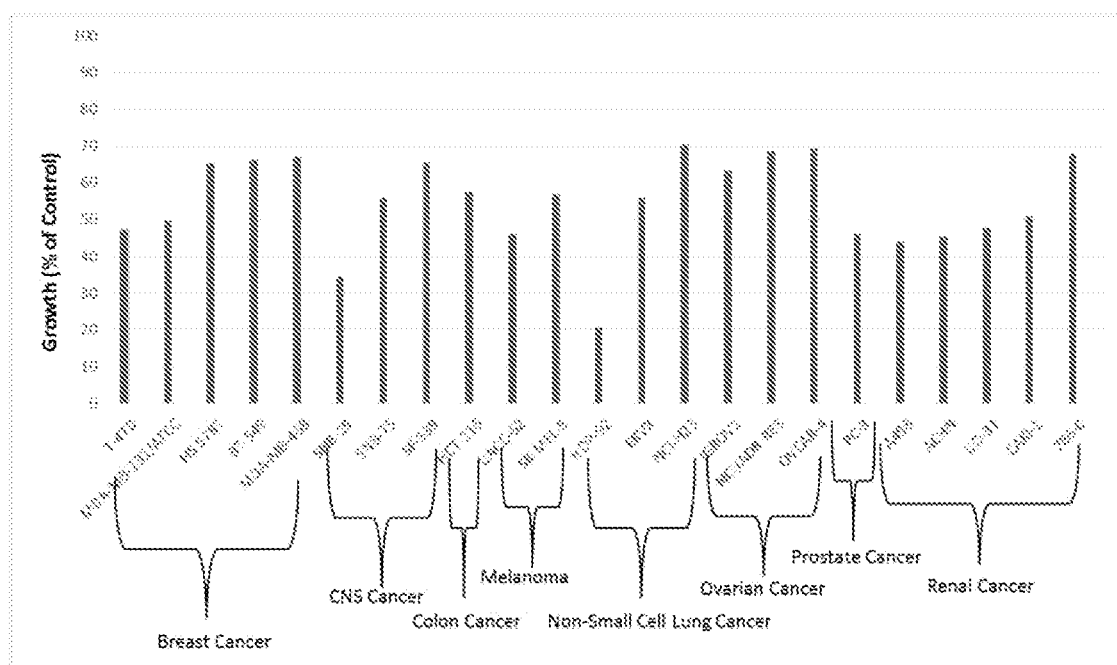
FIG. 2: Inhibition of breast cancer cell lines: T-470, MDA-MB-231/ATCC, H5578T, BT-549, and MDA-MB-468; the CNS cancer lines: SNB-19, SNB-75, SF-539; Colon cancer cell line HCT-116; Melanoma cell lines: UACC-62 SK-MEL-5; non-small cell lung cancer cell lines: HOP-92, EKVX, NCI-H23; ovarian cancer cell lines IGROV1, NCI/ADR-RES, OVCAR-4; prostate cancer cell line PC-3; and renal cancer cell lines: A498, ACHN, UO-31, CAKI-1, and 786Q by BCN057.

A cancer cell survival profile on multiple leukemia cell lines was conducted on BCN057 as described in Monks, A.; Scudiero, D. A.; Skehan, P.; Shoemaker, R. H.; Paull, K. D.; Vistica, D. T.; Hose, C.; Langley, J.; Cronice, P.; Vaigro-Wolf, M.; Gray-Goodrich, M.; Campbell, H.; Mayo, M. R. JNCI, J. Natl. Cancer Inst. 1991, 83, 757-766. The assay shows percent growth over 48 h at 10 uM BCN057 vs control (no drug). The drug was inhibitory towards Leukemia and also towards prostate and kidney cancer (data not shown). Examples of cell lines include: SR; large cell immunoblastic lymphoma, RPMI-8226; plasmacytoma and myeloma, MOLT-4; acute T lymphoblastic leukemia, K562; erythromyeloblastoid leukemia or chronic myeloid leukemia cell line, HL-60 (TB); acute myeloid leukemia, CCRF-CEM; T cell lymphoblast-like cell line. Results are shown in FIG. 1 for RPMI-8226, K-562, and CCRF-CEM In addition to leukemia and lymphomas, other tumor cell lines were susceptible to the BCN057 such as breast cancer, lung carcinoma, prostate, central nervous system (CNS), melanoma, ovarian, prostate, and renal and colon cancer (FIG. 2).

The experiment was further conducted on the breast cancer cell lines: T-470, MDA-MB-231/ATCC, H5578T, BT-549, and MDA-MB-468; the CNS cancer lines: SNB-19, SNB-75, SF-539; Colon cancer cell line HCT-116; Melanoma cell lines: UACC-62 SK-MEL-5; non-small cell lung cancer cell lines: HOP-92, EKVX, NCI-H23; ovarian cancer cell lines IGROV1, NCI/ADR-RES, OVCAR-4; prostate cancer cell line PC-3; and renal cancer cell lines: A498, ACHN, UO-31, CAKI-1, and 786Q. Results are shown in FIG. 2, where the Y-axis represents percent growth relative to a control of the same cell type untreated (i.e., 100% in each case)

It is demonstrated that BCN057 causes significant inhibition of the cancer cell growth, showing a direct effect on the cancer itself, and not only the conditions caused by treatments for cancer. This effect is unexpected for this compound.

In vitro studies have shown the drugs can inhibit cancer cell proliferation. The cancers affected include renal cancer, prostate cancer, non-small cell lung cancer, breast cancer, colon cancer, ovarian, leukemia, skin cancer such as melanoma, central nervous system cancers including pediatric brain cancers and adult brain cancers. Within this class of cancers, in particular the drugs show important inhibition of epithelial cancers such as colon, breast and oral cancers while protecting normal tissue such as in oral mucositis, proctitis and mucositis of the intestine.

Example 2: Effect on Platelet Count

Figure 3:
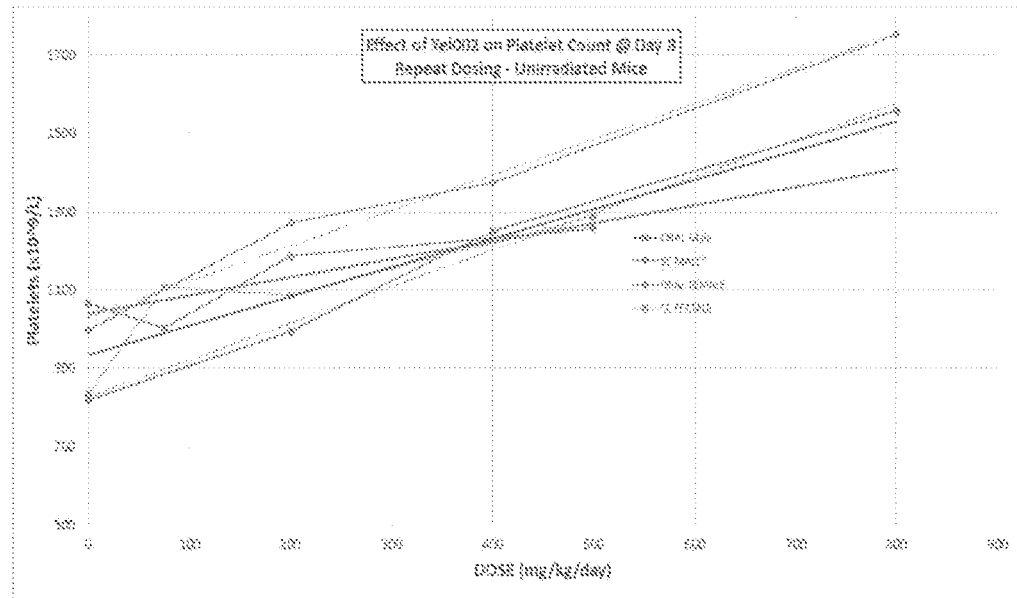
FIG. 3 is a graph of the amount of blood platelets from plasma (mouse) demonstrating through multiple doses and multiple routes of entry that the drug stimulates platelet production rapidly.

Normal mice were treated with BCN057 for eight days by oral administration or subcutaneous injection. Dose groups included 75 mg/kg/day, 200 mg/kg/day, 400 mg/kg/day, 500 mg/kg/day, and 800 mg/kg/day BCN057 induces platelet production in a dose dependent fashion. FIG. 3 is a graph of the amount of blood platelets from plasma (mouse) demonstrating through multiple doses and multiple routes of entry that the drug stimulates platelet production rapidly.

Example 3: Restoration of Cytokines after Irradiation

Mice were irradiated on Day 0. Animals were dosed with drug for 7 consecutive days (Day 1 to 7) at 200 mg/kg SC, with terminal blood collection on Day 8. Plasma from 3 mice was pooled for each condition Y axis represents relative absorbance units.

The plasma was tested with the Mouse Cytokine panel ELISA Array panel—by SIGNOSIS™

Figure 4:
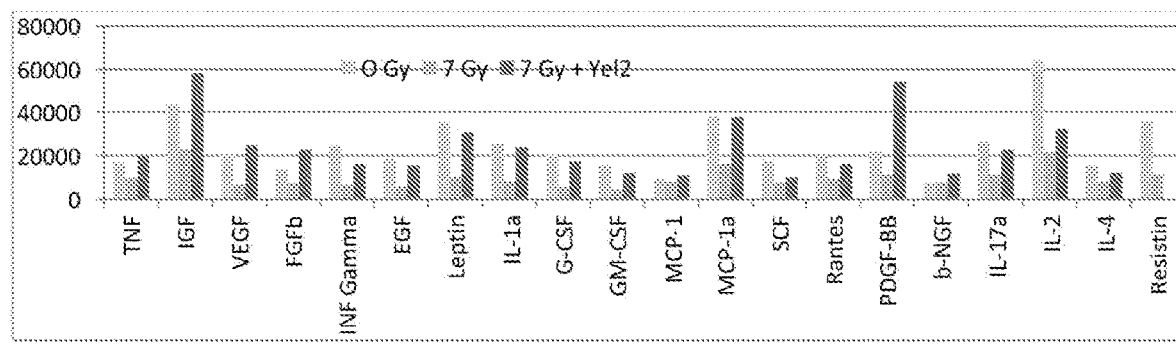
FIG. 4: Cytokine panel for mice treated with BCN057.
Figure 5:
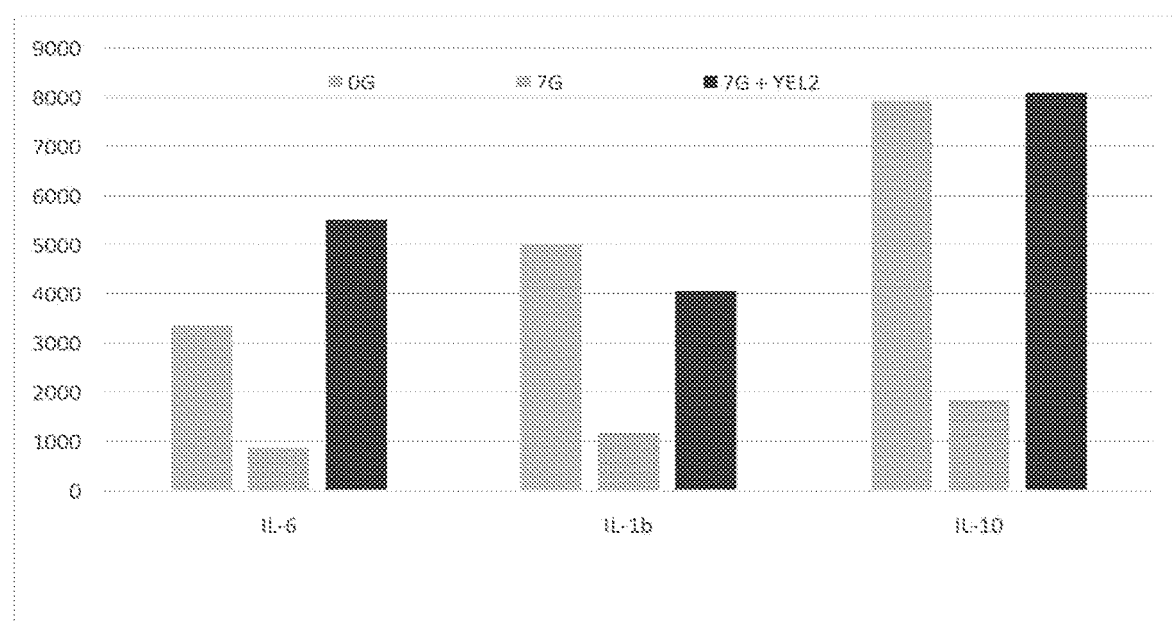
FIG. 5 shows the cytokine analysis of plasma from mice treated with nothing (marked as 0G above), 7 Grey radiation (7G) and 7G+BCN057.

Results are shown in FIGS. 4 and 5. There is a general trend of restoring cytokines to levels similar to control with exceptions. PDGF is important for restoration of mesenchyme and endothelial cells along with FGF. IL-6 and IL-10 are anti-inflammatory cytokines while GCSF and GMCSF affect macrophage infiltration and activation. FIG. 5 shows the cytokine analysis of plasma from mice treated with nothing (marked as 0 G above), 7 Grey radiation (7 G) and 7 G+BCN057). A restorative phenotype is observed in the presence of the drug similar to that of the control group receiving no radiation vs the group receiving radiation alone. This is important for inflammatory disorders as well as fibrotic disorders BCN057 alters key cytokines in blood to prevent an inflammatory condition. Analysis of the cytokines in animals treated with the drug after injury by radiation for example; there is a general theme of restoring cytokines to levels similar to control with some exceptions. IGF: known implications in gastrointestinal inflammatory diseases PDGF is associated with wound healing and tissue repair. Known to restore enterocytes and intestinal cell replacement. PDGF is also known to restore mesenchyme and endothelial cells as well. PDGF levels being high in the presence of the drug may also explain platelet production. FGF: restoration of mesenchyme and endothelial cells. IL-6 and IL-10 are anti-inflammatory cytokines involved in amelioration of sepsis following GI radiation injury or GI inflammatory disorders. GCSF and GMCSF promote or induce macrophage infiltration and activation in intestine. EGF is an intestinal epithelial growth factor. In most cases, BCN057 restores the cytokine profile to similar to that of the control on day 1.

Example 4: Hematopoietic Recovery Following Irradiation

Recovery of the hematopoietic system following 6 Gy irradiation of C3H mice (n=4) with BCN057 treatment (s.c.) at 24, 48, 72, 96, and 120 hrs. RBC- red blood cells (M/uL), HB-hemoglobin (g/dL), and HCT-hematocrit (%). B: recovery of the hematopoietic system following 6 Gy irradiation of C3H mice (n=4) with BCN057 treatment (s.c.) at 24, 48, 72, 96, and 120 hrs. WBC-white blood cells, NE-neutrophils, LY-lymphocytes. C: platelet (PLT) recovery following 6 Gy irradiation of C3H mice (n=4) with BCN057 treatment (s.c.) at 24,48,72,96, and 120 hrs; $p<0.05$ with a 1-tail, Student t-test. The drug shows evidence of improving hematopoietic recovery. See FIGS. 8 to 10.

Example 5: Formulations

Several formulations were developed to solubilize BCN057 in aqueous solution at physiologically compatible pHs. These include 100 mM methanesulfonic acid/10% povidone (PVP); 100 mM MSA/2% benzyl alcohol/2% N-methylpyrrolidone (NMP); and, 100 mM MSA/10% ethanol/1% Poloxamer 188. The addition of 100 mM lactic acid also improved solubility for these mixtures. Also, solutions containing 30 wt % Captisol (SBE-beta-CD) and 100 mM MSA yielded excellent solubility at up to pH 4.1.

Several suitable formulations were developed for intravenous, subcutaneous and oral delivery of therapeutic levels of BCN057. These include 30 wt % Captisol (SBE-beta-CD) and 100 mM MSA at pH 4.1 (adjusted with 1.0 N NaOH).

Furthermore, analytical methods to determine purity and quantity in drug product were created which included HPLC Assay and Impurities using a reverse-phase gradient method with C18 column and UV detection at 210 nm; osmolality and pH using standard techniques.

Example 6: BCN512 and Lung Fibrosis

Our goal is to develop a drug to protect lung from ionizing radiation that is administered subcutaneously and has a favorable risk/benefit profile when administered 24 hours or later after radiation exposure. The drug, BCN 512, originally discovered in the UCLA CMCR, is a novel drug that emerged from high-throughput screening of small molecule libraries, and is now under investigation as a radiation injury mitigator. In our efforts to develop the drug as a lung MCM to treat the Delayed Effects of Acute Radiation Exposure (DEARE), we use the C57BL/6 and C3H mouse models. These models appear to recapitulate human lung fibrosis and pneumonitis, respectively, based upon the distinct sensitivity of the two strains (1, 2). Survival and histology data suggest that in these rodent models, BCN512 is effective in ameliorating lung fibrosis and pneumonitis.

Data: Mice (8 per group) exposed to single whole thoracic lung irradiation (18 Gy at 0.6 Gy/min using an AEC Gammacell® 40 Cs-137 source) subcutaneous administrations of 512 in Cremophor on days 1-5 post-irradiation at 5 mg/Kg improved overall survival from pneumonitis and lung fibrosis at 90 days and 160 respectively. Radiation fibrosis is a progressive, dose-related, late complication of radiation exposure, with animals and humans surviving for some time with non-lethal damage. FIG. 18 shows that after 14 Gy, which is not lethal for most mice, the acute delivery of BCN512 mitigates against the development of this late disease. 512 works by altering the inflammatory infiltrate into the lung. By day 160 after LTI the mature macrophage cell content is greatly decreased as a result of acute drug treatment.

Because the side effects of Cremophor are undesirable for an MCM candidate, alternative formulations are being tested for further development of 512 for the lung DEARE indication. Once such formulation using Deoxycholate shows plasma exposure (FIG. 6A) when given subcutaneously (SC) and also shows good efficacy in total body irradiation experiments indicating that the drug has retained its mitigation properties.

In addition, other important prototype formulations are being developed in partnership with Particle Sciences, Bethlehem, Pa., to create nanoparticle formulations of the drug substance. Furthermore, nanoparticle drug substances are known to more preferentially distribute to sites of inflammation (3) which may be favorable in this case 512 is a lead candidate for the development of a drug for delayed effects of radiation exposure in lung. Further work will include extensive testing in lung models along with characterization of the toxicology, pharmacology and metabolism of the drug product before pivotal non GLP animal studies.

Example 7: Radio-mitigation of Normal but not Tumor Tissue

One of the major concerns of the Food and Drug Administration for the application of radiation mitigators in RT is that if an agent can protect normal tissue from radiation damage, it may also protect tumor tissues. In our phase I proposal, we used syngeneic, allogeneic, and xenograft lung tumor models to show that the drug did not accelerate the growth of tumor lung colonies in vivo with or without LTI (FIG. 3A-B). The syngeneic model of artificial metastasis used Lewis lung (LLC) tumors, and since LLC also grow in C3H mice, this could be employed as an allogeneic model. C57Bl/6 and C3H mice were injected i.v. with $5\times10^4$ tumor cells. Subcutaneous drug injections were started on day +3 when the tumors were established in the lung in order to bias the experiment in favor of tumor growth promotion. The dose regimen was arbitrarily assigned to a dose of 20 mg/kg for 5 days. LTI was started on day 4, with 4 Gy doses administered daily for 3 days. This is higher than conventional 2 Gy to compensate for the more rapid growth of murine tumors, but is still well within the range used clinically in hypofractionated therapy.

Treatment with BCN512 significantly (P<0.05) decreased the number of lung tumor colonies on day 14 by 20% in both C3H and C57 mouse strains, and the colonies in both strains were smaller in size than control. LTI alone decreased the number of co DNA repair lonies by 40%. Extensive analysis of the drug doses that would be optimal for exerting effects on tumors in the radiation setting are still needed, but there is no evidence for enhanced tumor growth as a result of radiation treatment with drug, and in fact exactly the opposite. We are therefore confident that BCN512 shows anti-tumor activity in vivo. FIG. 3C shows additional data from the A549 human NSCLC cell line. Thirty-two nude mice were injected intravenously with 5×104 human A549 adenocarcinoma cells on day 1. The drug was administered starting at day 3; 20 mg/kg BCN512 was injected subcutaneously once daily for 5 days. Fractionated radiation was started on day 4, with 4 Gy LTI administered daily for 3 days. Tumors developed very slowly, so the mice were sacrificed on day 72 and the number of nodules in the lungs were counted. There was considerable variation in the irradiated group, with a tendency for lung irradiation to increase the number of tumor colonies. This is not a unique observation that may be ascribed to radiation-induced myeloid cell mobilization. In any event, BCN512 did not increase the number of tumor colonies, and if anything decreased the count, especially in the irradiated group.

Figure 6:
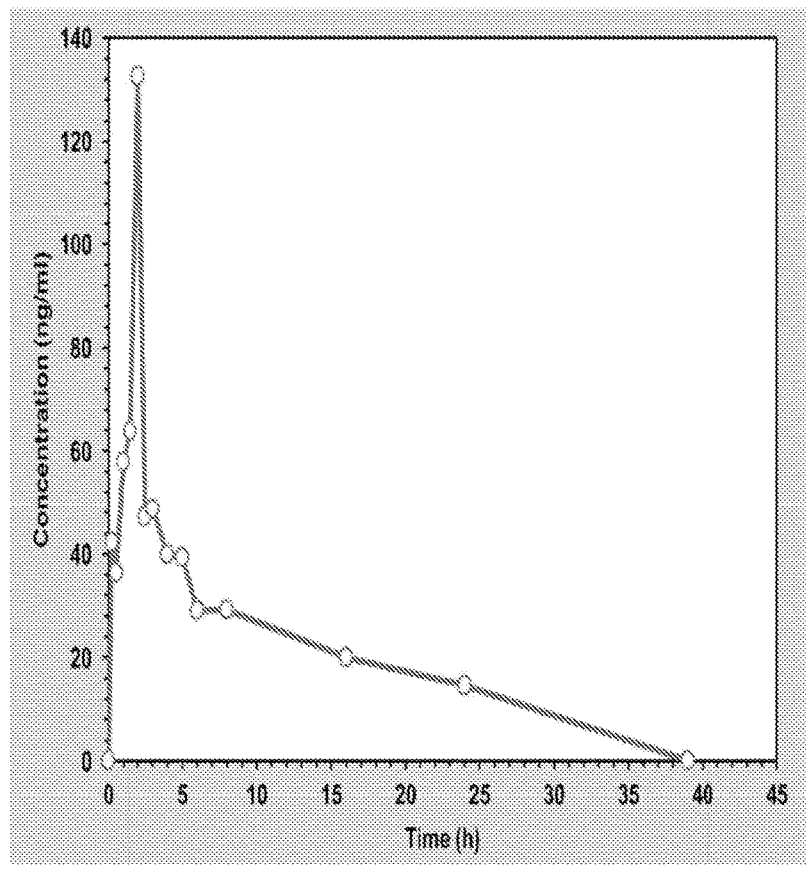
FIG. 6A: Pharmacokinetic profile for C57BL/6 male mice receiving a 10 mg/kg sc injection of 512 in a low % deoxycholate formulation. Cmax observed is 132.5 ng/ml with a Tmax observed at 2 hours.
FIG. 6B: BCN512 did not increase the number of tumor colonies
Figure 6:
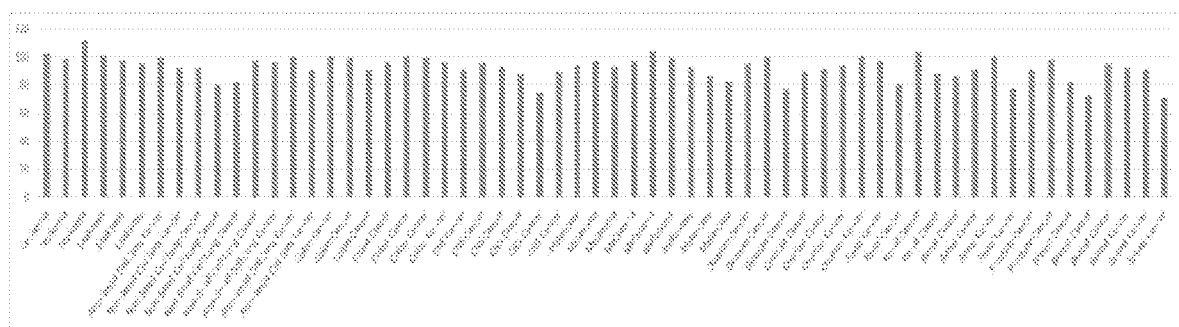
Figure 7:
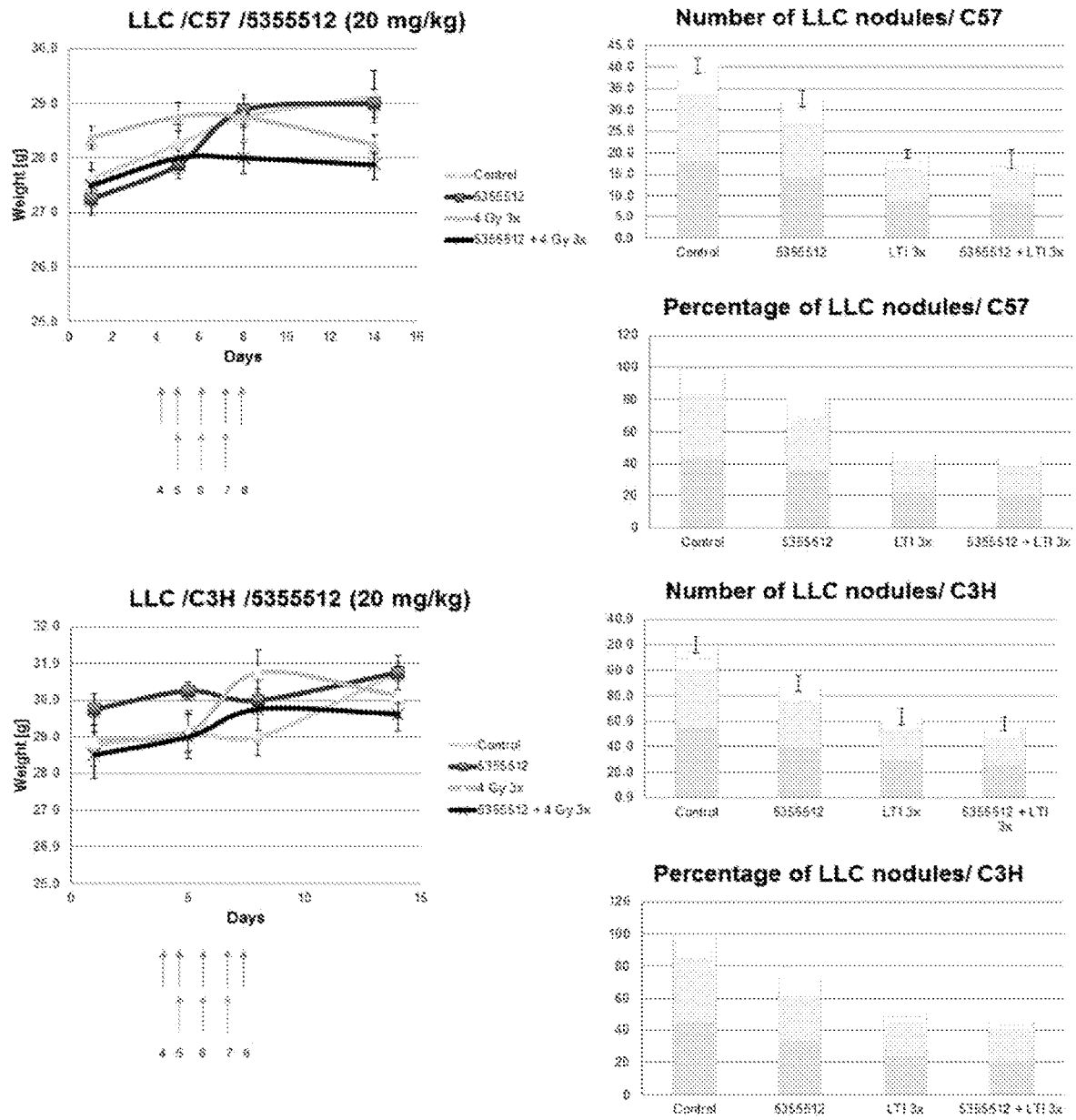
FIG. 7A-D: Tumor metastasis models of the number of metastatic tumor nodules in C3H, C57B16, and nude mice. (A) weight (C57) over time. (B). Number of LLC nodules (C57) and percentage of LLC nodules. (C) weight (C3H) over time. (D). Number of LLC nodules (C3H) and percentage of LLC nodules.

See FIG. 6B. The NCI screening procedures were as described (1) as were the origins and processing of the cell lines (1, 2, 3, 4). Briefly, cell suspensions that were diluted according to the particular cell type and the expected target cell density (5000-40,000 cells per well based on cell growth characteristics) were added by pipet (100 μL) into 96-well microtiter plates. Inoculates were allowed a preincubation period of 24 h at 37° C. for stabilization. Dilutions at twice the intended test concentration were added at time zero in 100-μ L aliquots to the microtiter plate wells. Usually, test compounds were evaluated at five 10-fold dilutions. In routine testing, the highest well concentration is 1×10-4 M, but for the standard agents the highest well concentration used depended on the agent. Incubations lasted for 48 h in 5% CO2 atmosphere and 100% humidity. The cells were assayed by using the sulforhodamine B assay (5, 6). A plate reader was used to read the optical densities, and a microcomputer processed the optical densities into the special concentration parameters defined later. Screening Procedures Leukemia; CCRF-CEM, HL-60(TB), K-562, MOLT-4, RPMI-8226, SR. Non-Small Cell Lung Cancer; 549/ATCC, EKVX, HOP-62, HOP-92, NCI-H226, NCI-H23, NCI-H322M, NCI-H460, NCI-H522. Colon Cancer; COLO 205, HCC-2998, HCT-116, HCT-15, HT29, KM12, SW-620. CNS Cancer; SF-268, SF-295, SF-539, SNB-19, SNB-75, U251. Melanoma; LOX IMVI, MALME-3M, M14, MDA-MB-435, SK-MEL-2, SK-MEL-28, SK-MEL-5, UACC-257, UACC-62. Ovarian Cancer; IGROV1, OVCAR-3, OVCAR-4, OVCAR-5, OVCAR-8, NCI/ADR-RES, SK-OV-3. Renal Cancer; 786-0, A498, ACHN, CAKI-1, RXF 393, SN12C, TK-10, UO-31. Prostate Cancer; PC-3, DU-145. Breast Cancer; MCF7, MDA-MB-231/ATCC, HS 578T, BT-549, T-47D, MDA-MB-468.

Example 8: Hematopoiesis

Both BCN057 and BCN512 activate Wnt signaling in stem cells promoting self-renewal and proliferation. Hematopoietic stem cells are also driven by wnt signaling and are thus stimulated by the drug.

Figure 8:
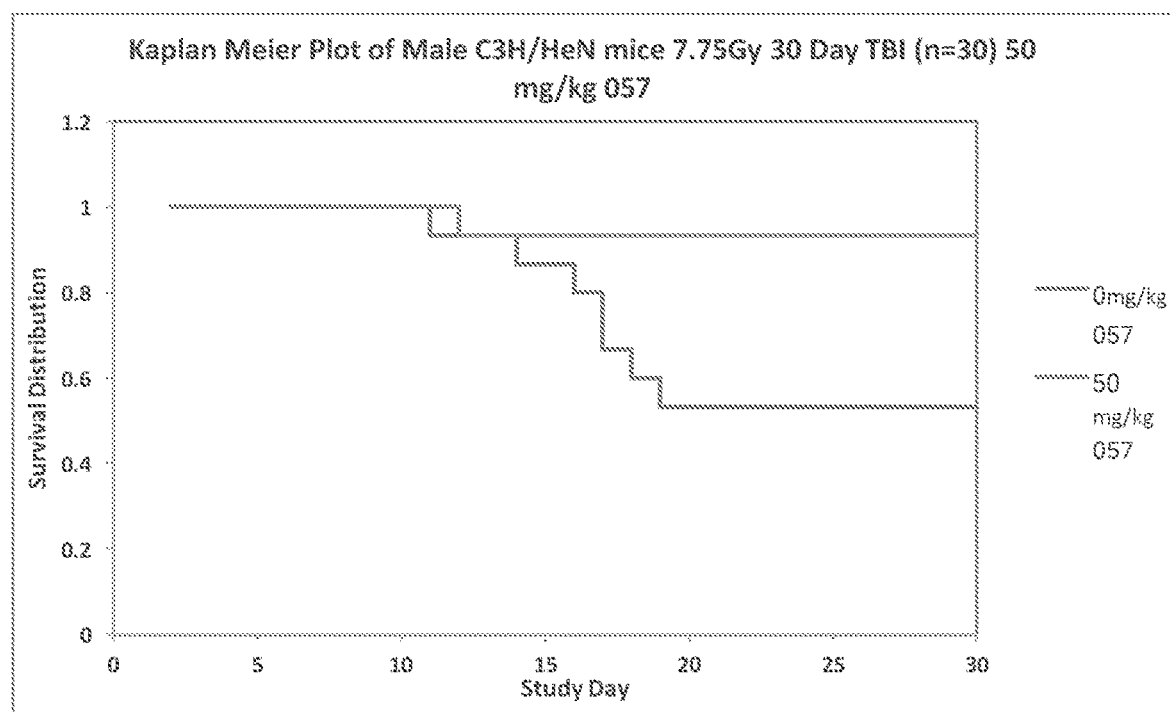
FIG. 8A-C: (A) Kaplan Meier Plot of Male C3H/HeN mice 7.75Gy 30 Day TBI (n=30) 50 mg/kg BCN057. (B). Kaplan Meier Plot of Female C3H/HeN mice 7.75Gy 30 Day TBI (n=10) 25 mg/kg BCN057. (C) Cytokine Profile in Plasma Male C3H/HeN mice 7.75Gy TBI Day 8 receiving BCN057.
Figure 8:
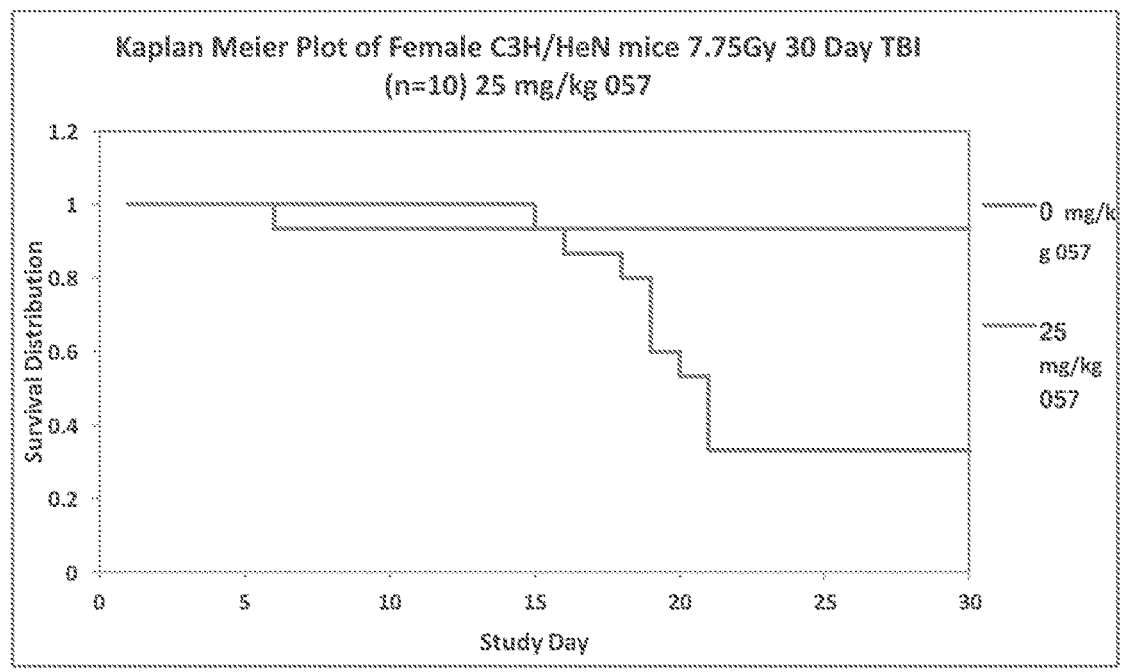
Figure 8:
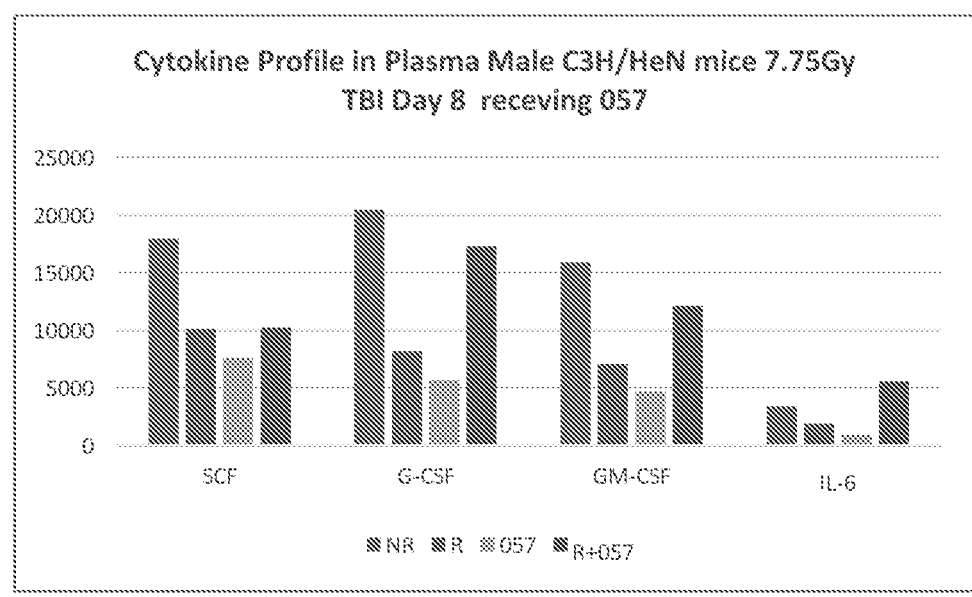
Figure 9:
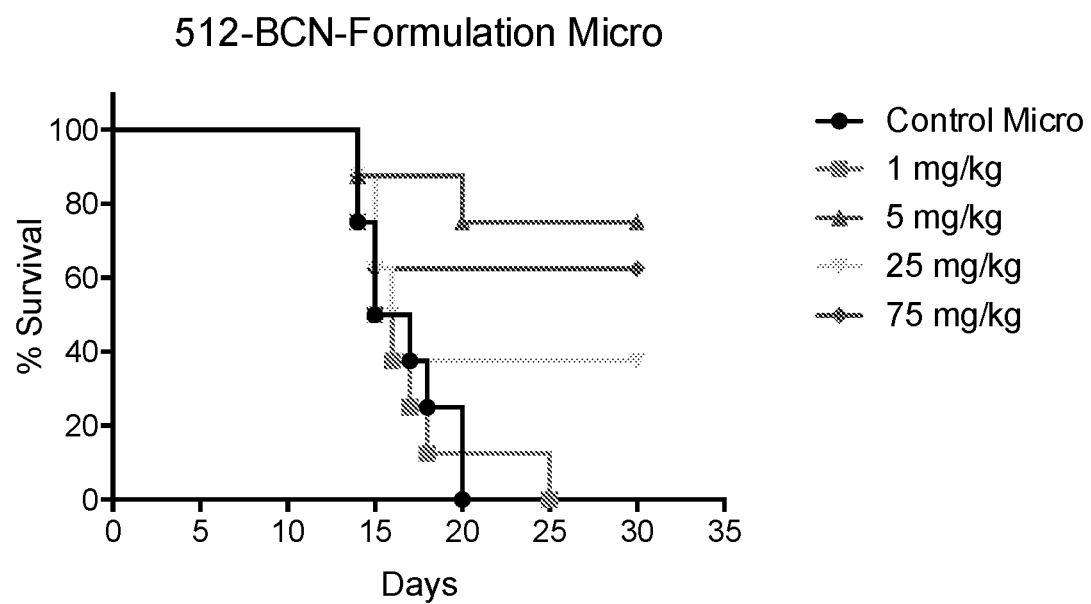
FIG. 9: BCN512 prevents hematopoietic suppression from total body irradiation in mice.

FIGS. 8 A-B show that BCN057 helps prevent hematopoietic suppression from total body irradiation in male and female mice. 7.75 Gy radiation is used to ablate bone marrow hematopoietic stem cells (HSCs) in these strains of mice. BCN057 is sufficient to prevent lethality from bone marrow suppression. Lethality from bone marrow suppression occurs in the 14-25 day region due to the life cycle of approximately 2 weeks for RBC and inability to replace them without HSCs FIG. 8 C shows that bone marrow-derived stem cells express hematopoietic cytokines IL3, I16, IL11, GCSF, GMCSF, LIF, MCSF, SCF, which are important for supporting long-term hematopoiesis. Plasma levels of, I16, GCSF, GMCSF, SCF are elevated after drug treatment and in conjunction with the radiation treatment indicating hematopoietic stem cells are effected FIG. 9 shows that BCN 512 prevents hematopoietic suppression from total body irradiation in mice. 7.73 Gy radiation is used to ablate bone marrow HSCs in the C3H strain of mice. BCN512 is sufficient to prevent lethality from bone marrow suppression from total body irradiation.

Figure 10:
FIG. 10: Bone marrow removed from mice treated with nothing (control) or 512, second from left.
Figure 11A:
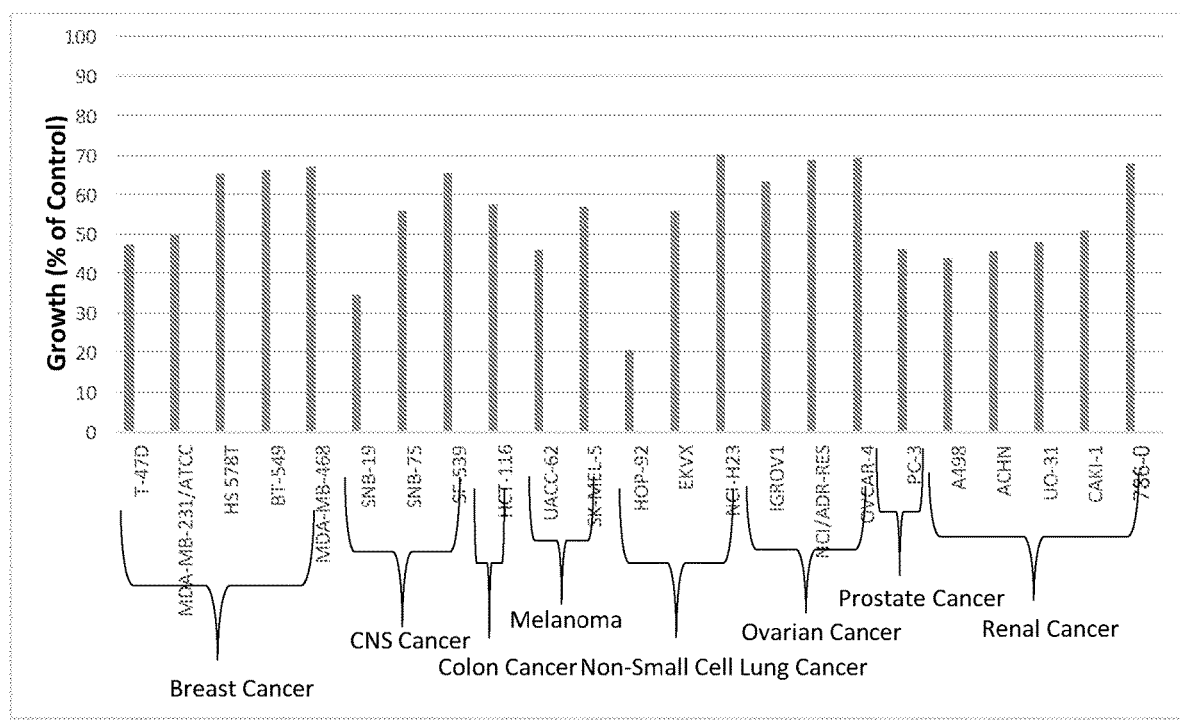

FIG. 10 shows that radiation ablates the bone marrow which exhibits as pale bone marrow devoid of RBC's (LTI). Finally, radiation (LTI) and BCN512 and LTI (last to right) show similar red color (hemoglobin) to control.

In summary, whole body irradiation studies are used to ablate the hematopoietic system (red blood cells, white blood cells and their progenitors along with stem cells from which they are all derived) in both humans and mammalian bone marrow. The bone marrow will become white due to a-cellularity and become unable to produce adequate red and white cells with a resulting death at a radiation dose that is specific for the hematopoietic system (other organs are not appreciably affected). The survival associated with these drugs without blood replacement along with the presence in plasma of bone marrow derived cytokines and/or platelet increase associated with the presence of the cells in the treated group vs the untreated group show the drugs promote hematopoiesis and prevent neutropenia in the case of insult to bone marrow by toxic agents.

Figure 12:
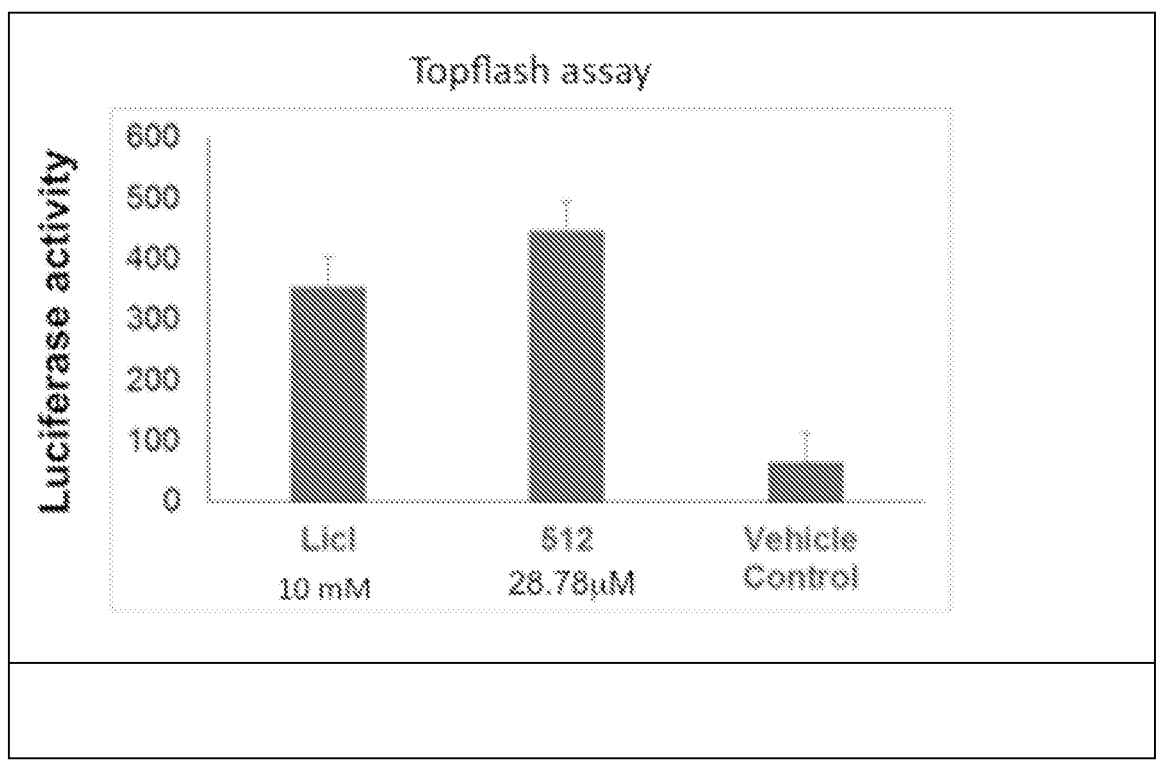
FIG. 12: BCN 512 treatment induced luciferase activity, indicating activation of canonical Wnt signaling.

Example 9: Fibrosis and Wound Healing 512 activates canonical Wnt-β catenin signaling: To determine the canonical Wnt activity induced by BCN-512 (28 μM), HEK293 cells possessing a TCF/LEF luciferase reporter construct were treated with BCN-512 or vehicle control. LiCl (10 mM) treatment was used as positive control for luciferase activity. Luciferase activity was determined after 24 h using a Dual-Luciferase® Reporter Assay System (Promega) as per manufacturer's protocol. HEK293 cells containing a FOPFlash construct were used as a negative control. BCN-512 treatment significantly increased luciferase activity in HEK293 cells compared with vehicle treated cells. The positive control LiCl also significantly increased luciferase activity (FIG. 12)

Figure 13:
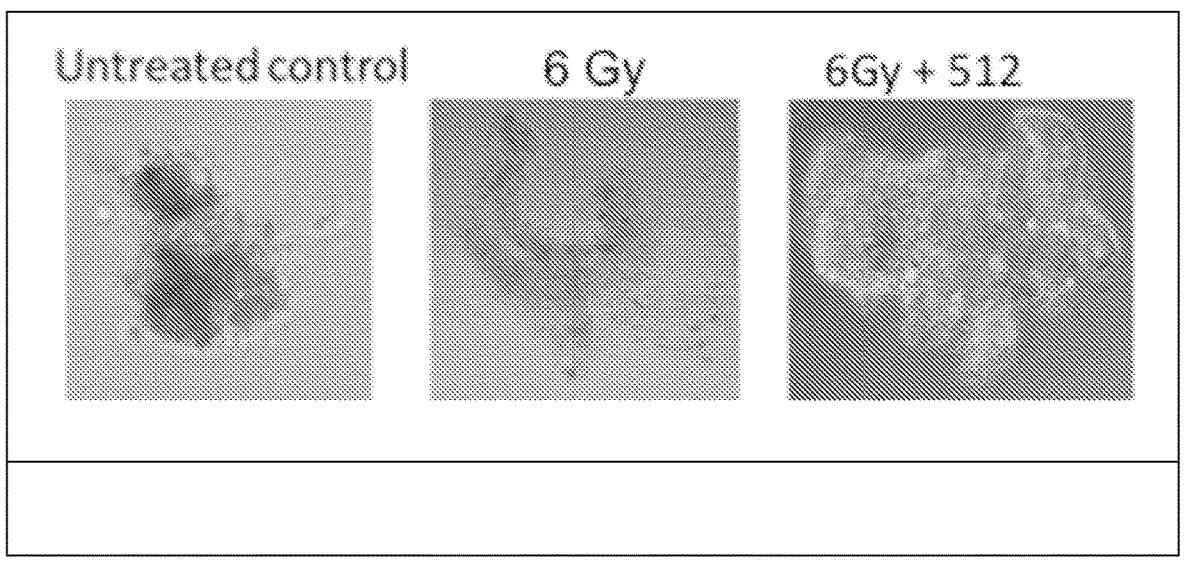
FIG. 13A-C: BCN-512 mitigates radiation-induced damage in lung organoids. Please note that in the untreated group, the organoid structure was completely lost within 72-96 h of radiation exposure.

512 induces lung organoid growth in ex vivo cultures: Ex vivo 3D organoid cultures are one of the best models for studying stem cell growth and proliferation because organoid growth depends primarily on the presence of stem cells. For these experiments, mice were euthanized by $CO_2$ or ketamine-xylazine administration and the abdominal aorta was exposed and exsanguinated. The thoracic cavity was opened, and the lungs were exposed. Blood was flushed from the lung vasculature by perfusion with 10 mL of sterile cold PBS through the right ventricle. The trachea was cannulated with a 24-G cannula, and 1.2 mL of 10 U dispase (BD) was then injected into the lungs. The trachea and lungs were removed from the chest en-block and incubated for 20 minutes at room temperature (RT). The lung lobes were dissected from the trachea, heart, and rest of mediastinal structures and then finely minced and incubated for 10 more min with 2 mL of dispase. The suspension was passed through an 18-G needle 4-5 times to help open the lung compartments. If sticky DNA was detected, 10-30 µL of 4 mg/mL DNase I (Sigma) was added to the cell suspension and incubated at 37° C. for 5 min. The cells were filtered through a 100-µ cell strainer (BD Biosciences) to obtain single-cell suspensions (SCS). Red blood cells were lysed using RBC lysing buffer. Lung epithelial cells were resuspended in lung 3D culture media and mixed 2:1 with Cultrex Reduced Growth Factor Basement Membrane Extract, Type 2 (BD Biosciences). Then, 150 µL were placed into 24-well plates and incubated at 37° C. incubator for 20-30 min to solidify the matrix. A total of 600 µL lung 3D culture media was added carefully to the side of the wells and kept in a 37° C. incubator. The media were changed 2-3 times per week Radiation exposure (6 Gy) inhibited organoid growth. However, treatment with BCN-512 (28 µM) at 1-hour postradiation exposure mitigated the radiation damage and induced lung organoid growth (FIG. 13)

Figure 14:
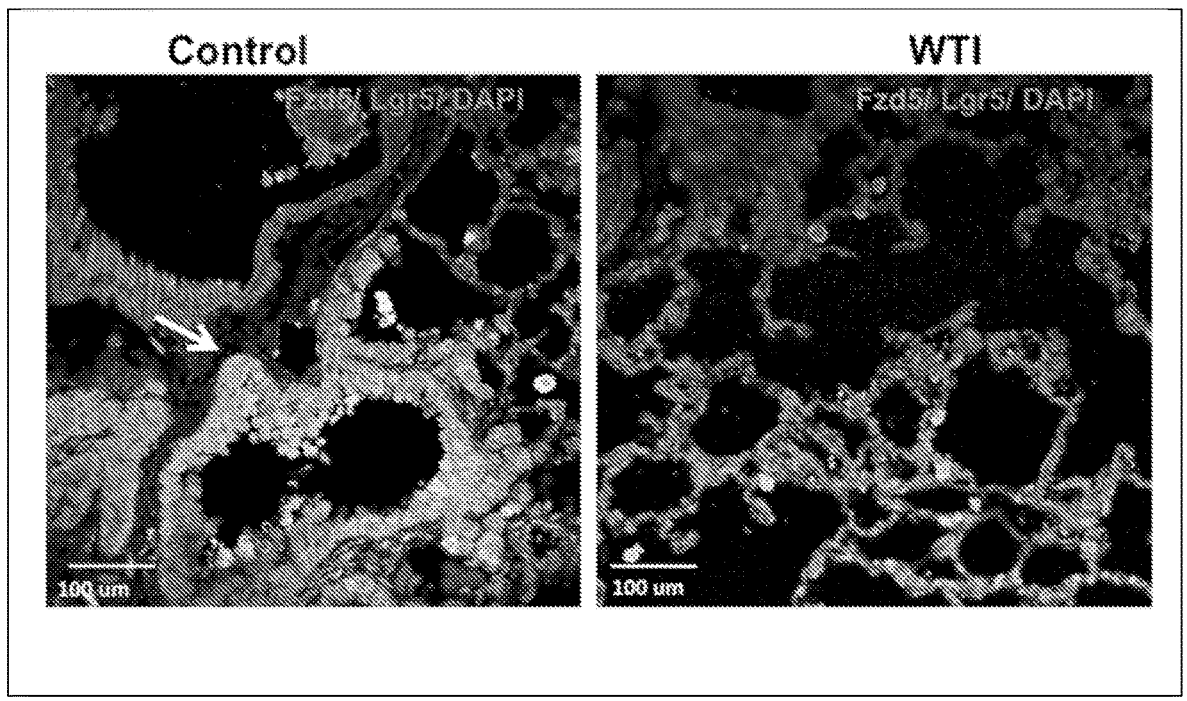
FIG. 14A-B: Lgr5 and Fzd5 receptors were co-localized in cells at the BADJ region. Lung epithelial sections from Lgr5-GFP-Cre-ERT mice were stained with chicken anti GFP antibodies (primary antibody; 1:200 dilution) and donkey anti-chicken 488 (secondary antibody; 1:200 dilution) to detect Lgr5 expression. To detect Fzd5 expression, sections were stained with rabbit anti-Fzd (primary antibody; 1:50 dilution) and donkey anti-rabbit 546 (secondary antibody; 1:200 dilution). Fzd5-positive cells are red and Lgr5-positive cells are green. Cells co-expressing both receptors are yellow in color (red+green) and are primarily located at the BADJ region, as indicated with an arrow.
Figure 15:
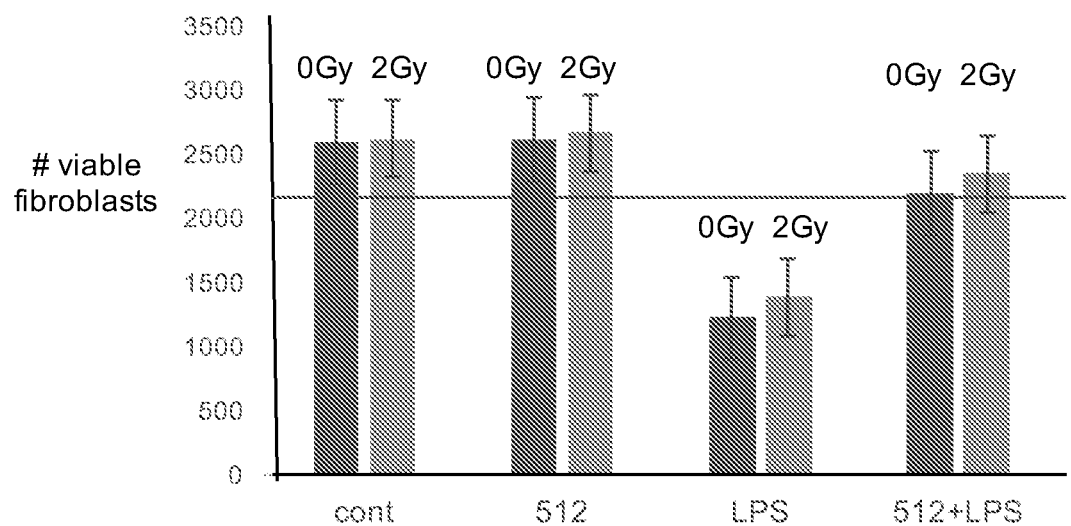
FIG. 15: Number of fibroblasts recovered from co-cultures with 25-fold more non-irradiated or 2 Gr-irradiated macrophages treated with diluent, BCN 512, LPS, or LPS+ BCN 512 after 3 days culture. The blue line is the no macrophage control.

Pulmonary epithelial cells co-express Lgr5 and Fzd5 receptors in progenitor cells located at the bronchoalveolar duct junction (BADJ): The Lgr5 receptor is associated with the Frizzled/Lrp Wnt receptor complex. R-Spondin1 is an intestinal mitogenic factor that binds to the Lgr5 receptor and activates Wnt-β catenin signaling Lgr5 and Wnt receptor expression in the mouse lungs was assessed by performing immunofluorescence staining of the mouse lung epithelium. Confocal microscopic images of mice lung epithelium clearly demonstrated the presence of Lgr5- and Fzd5-positive cells (FIG. 14). It was noted that the Lgr5 and Fzd5 receptors were co-expressed in the BADJ region, which is enriched in progenitor cells. However, most Lgr5- and Fzd5-positive cells disappeared within 5-7 days of irradiation with 18 Gy whole-thorax lung irradiation (WTLI) (FIG. 14).

Example 10: Modulation of Macrophage Function

Myeloid cells were used to study the mechanism of action of the radiomitigator BCN-512 based on the following previous observations:

1. Lung irradiation activates macrophages both short- and long-term (up to 6 months)

2. BCN-512 greatly increases the number of immature myeloid cells that appear after whole body irradiation (WBI) and WTLI. They co-express CD11b, Ly6G, and Ly6C, and are required for mitigation by BCN-512, at least after WBI.

3. The mitigation of radiation lung damage by BCN-512 after LTI is accompanied by a decrease in inflammatory macrophage content and phenotypic markers in the lung on day 150.

4. 512 decreases the amount of pro-inflammatory cytokines released by inflammatory peritoneal macrophages in response to stimulation with LPS in vitro, suggesting that macrophage function is modulated.

5. The mitigation of radiation lung damage by BCN-512 is associated with an unexpected increase in anti-tumor activity; we suspect that this also will be mediated by functional changes in the macrophage population.

Because of the focus on lung fibrosis, we examined the effects of irradiation on macrophages in terms of their ability to modulate fibroblast responses. We then used the most accepted and studied model of inflammatory macrophages (stimulated peritoneal exudate cells), which is also the model we used to show that BCN-512 affected pro-inflammatory cytokine production. The following in vitro experiments demonstrate that BCN-512 can affect the function of macrophages by decreasing the activation status and cytotoxicity of LPS-treated macrophages. In addition, BCN-512 blocks the ability of irradiated macrophages to stimulate fibroblast proliferation. The ability of BCN-512 to reprogram macrophages is likely highly relevant to its ability to mitigate radiation induced fibrosis and tissue damage Cell proliferation was used as a sensitive in vitro endpoint because it can also be used to detect cell death. Cells were labeled with the fluorescent dye CF SE, which becomes diluted as the cells proliferate over time. We performed a series of experiments using tumor cell lines to validate the assay and determine the effective ratios of macrophages to target cells (not shown) before performing experiments with normal early-pass murine embryo fibroblasts. To study the effects of BCN-512 and macrophages on fibroblast cell proliferation and death, irradiated (2 or 6 Gy) macrophages and fibroblasts were added at various ratios. Normal mouse fibroblasts were labelled with CF SE and added to the macrophages in 96-well plates. BCN-512 (10 µM) and/or LPS (1 µg/mL) or diluent were then added, and the plates cultured for 1, 2, or 3 days. The purpose of the LPS was to activate the macrophages. BCN-512 was added 1 hour after LPS, which was added immediately after irradiation The data showed that the fibroblasts divided every 15 hours. Low ratios of non-irradiated macrophages at low ratios had little or no effect on fibroblast proliferation at any time point. However, at ratios of 20:1 or 25:1, treating macrophages with LPS made them cytotoxic to fibroblasts (FIG. 19). This could be attributed to growth arrest and fibroblast cell-killing by activated macrophages, since LPS alone had no direct effect on fibroblast proliferation or viability. There was no difference between the groups of irradiated and non-irradiated macrophages, but BCN-512 practically abolished the toxicity associated with LPS treatment.

Figure 16:
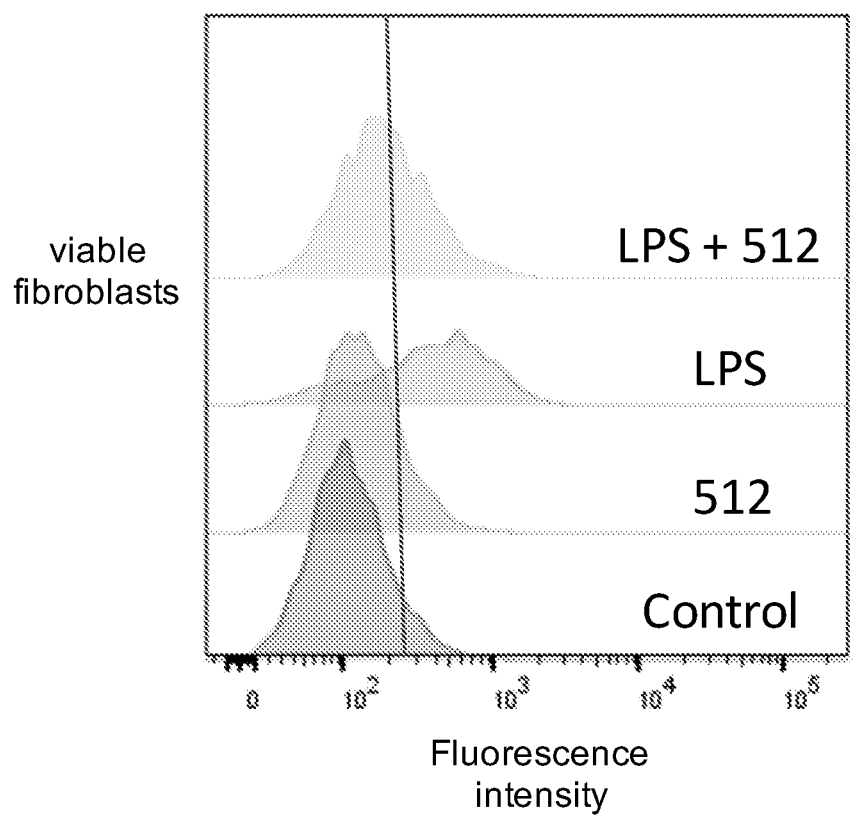
FIG. 16: Flow cytometry profiles of CFSE-labeled fibroblasts co-cultures with macrophages at a ratio of 25:1 for 3 days in the presence of diluent, BCN 512, LPS, or LPS+512. The fluorescence intensity decreased as the fibroblasts proliferated. Non-activated control macrophages actually stimulate fibroblast proliferation; the blue line represents no macrophage control. In contrast, activation with LPS caused the equivalent of a 1-day growth arrest and decreased viability.
Figure 17:
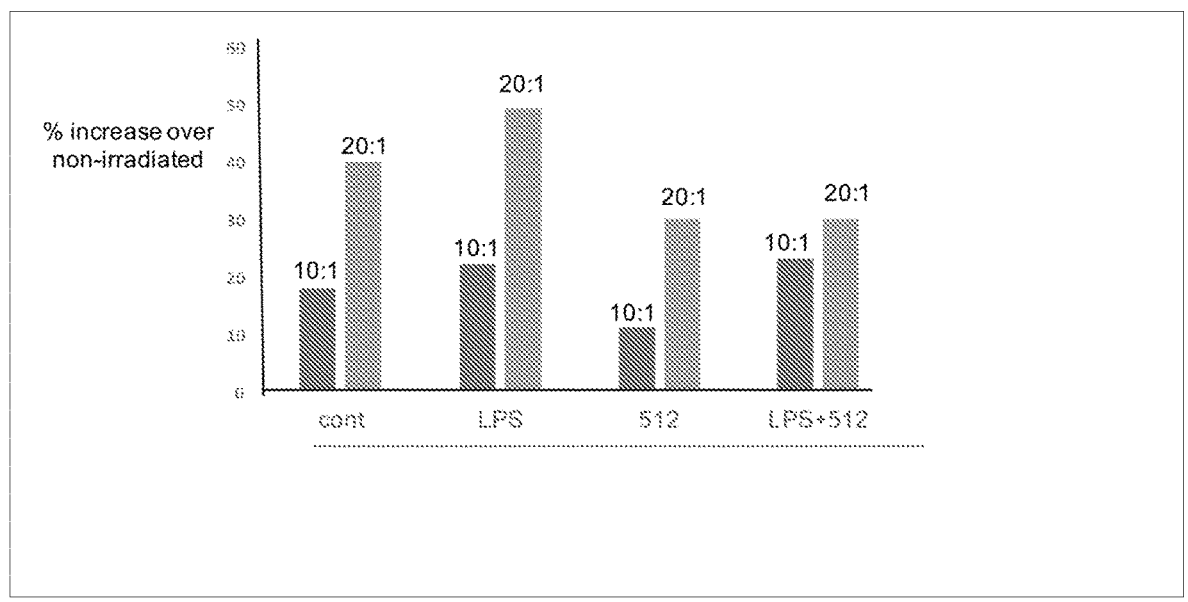
FIG. 17: The ratio of viable fibroblasts in irradiated (6 Gr) and non-irradiated macrophage co-cultures on day 3. Irradiation increased the ability of macrophages to support fibroblasts, and 512 decreased this effect of irradiation.

These findings are consistent with the concept that BCN-512 modulates macrophage function to suppress their inflammatory action; this requires at least 2 days of co-culture, as shown in FIG. 16. FIG. 16 also shows the tendency for normal macrophages to enhance the rate of fibroblast proliferation in vitro. In addition, 2 Gy irradiation enhanced this supportive action, although the results were not statistically significant. After 6 Gy macrophage irradiation (FIG. 17), the number of viable fibroblasts clearly increased by 30-50% in all cases by 3 days; the addition of BCN-512 seemed to neutralize this function FIG. 18 shows that local thoracic radiation (14.5Gy) of mice induces lung damage in the absence of BCN057. A: Lung histology of C57BL/6 mice receiving local thoracic radiation (radiation of the lung area) presenting a focal area of increased cellularity and edema on the upper left quadrant. Adjacent to this is increased cellularity (the lacey patterning). The lower right quadrant, emphysema is present with large clear areas indicating where alveoli have collapsed to present large open areas. B. Histopathology of C57BL/6 mouse lung under identical radiation treatment as A, but also treated with 5 mg/kg BCN512 once per day every 24 hours for 5 doses. Lung tissue is normal with no evident emphysema or edema or hyper cellularity or immune infiltrate.

FIG. 19 shows lung fibrosis: A, B are differing whole lobe sections from the same animal lung having received 14.5Gy local thoracic radiation (Day 120 after irradiation treatment). In both lobes, significant collapse of alveoli can be seen along with hyper cellularity (dark areas) and pronounced emphysema (large open areas) presenting fibrosis. C, D are separate lobes from the same animal treated identically as above but receiving BCN512 at 5 mg/kg daily for 5 days after 14.5Gy local thoracic radiation. Absent are the large lesions and pronounced fibrosis.

In summary for the above data, these in vitro experiments demonstrated that BCN-512 can affect the function of macrophages. It decreased the activation status and cytotoxicity of LPS-treated macrophages. For non-LPS treated macrophages, BCN-512 blocked the ability of irradiated macrophages to stimulate fibroblast proliferation. Fibroblast proliferation is macrophage dependent and 512 inhibits this macrophage function. The ability of BCN-512 to reprogram macrophages is likely highly relevant to its ability to mitigate radiation damage The absence of late effects in fibrosis from animals from long term radiation (observing from long term studies of the total body irradiation studies) along with the reduction of fibroblasts indicate these drugs are effective at preventing fibrosis and inflammation from both radiation or chemical means (LPS). Organoid structures are grown from stem cells to differentiate into the features of the organ they came from. The drugs activate wnt signaling of which, stem cells are a critical target population of cells that respond to wnt by self-renewal and differentiation. Stem cells are important for the repair and regeneration of tissues that are damaged and therefore these drugs preserve stem cells to allow for normal tissue repair. In the normal case, these stem cells are destroyed by radiation or chemotherapy for example which allows inflammatory macrophages and immune infiltrates to come in and remodel the tissue with consequent fibrosis in the late stage.

Example 11: Dermal Wound Healing

Figure 20:
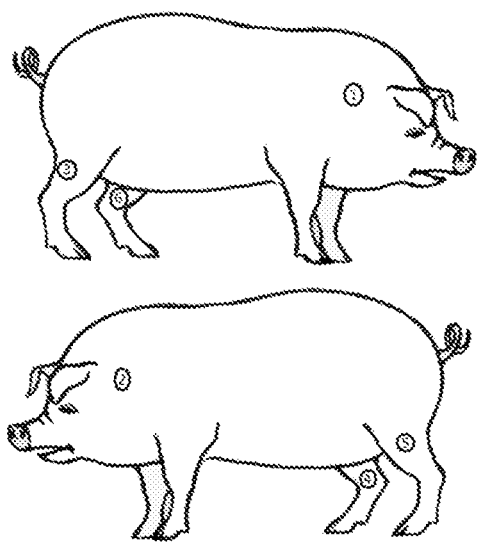
FIG. 20: Radiation sites for wound healing experiments.
Figure 21:
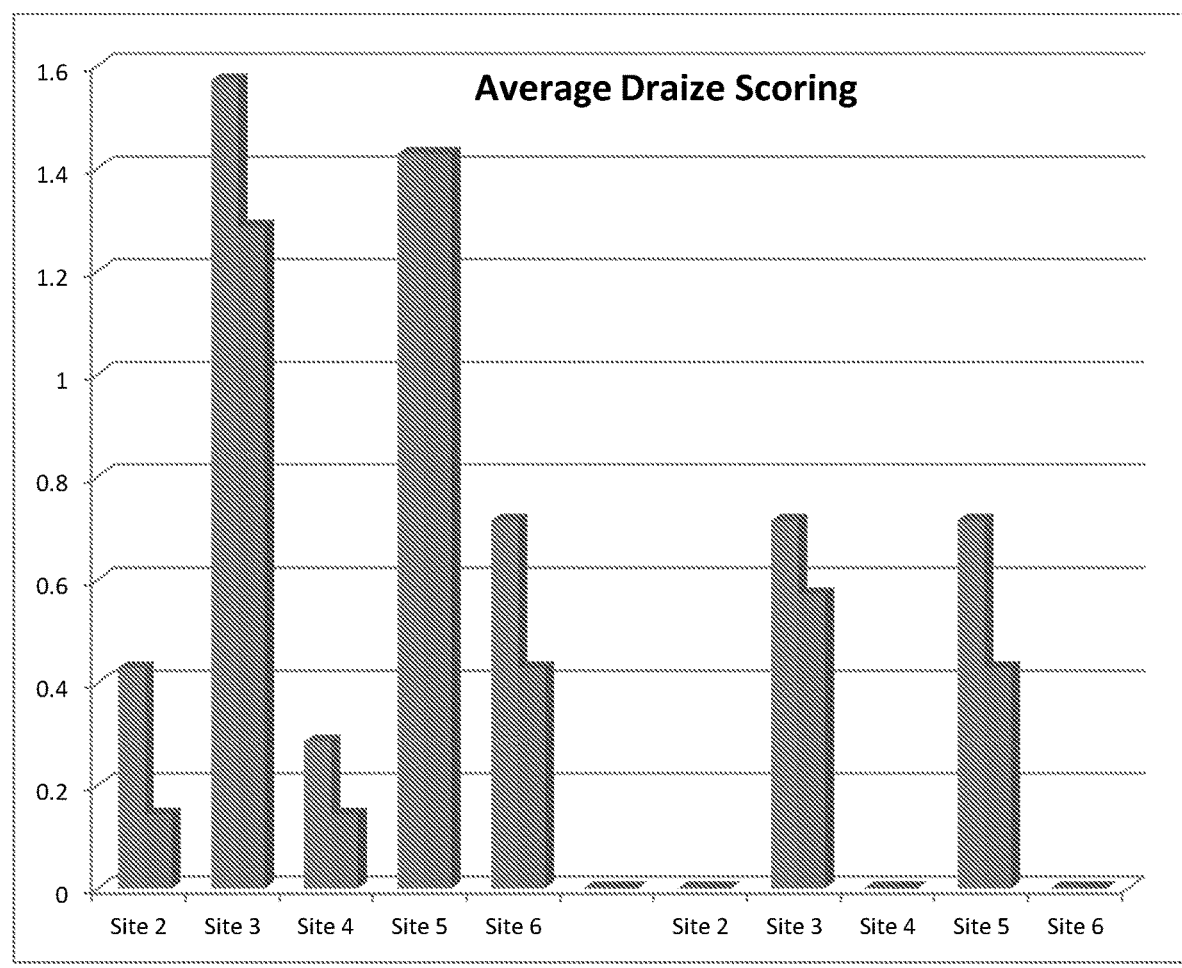
FIG. 21: Average Draize Scoring. Plot of difference between Erythema development (blue) (left 6 columns) and Edema (right 6 columns). Radiation treatment alone is blue and BCN057 treatment is red (right column pair).

FIG. 20 shows the sites of radiation described in Table 2.

TABLE 2

Average Draize scoring for treatment of control, (no radiation), BCN512 or BCN057 at day 15 post dermal radiation receiving radiation doses of 25, 35 and 45 Gy according to table Y below. The day of irradiation will is Day 0. Animals receive localized irradiation on Day 0. A total of six sites, measuring approximately 4 × 4 cm, are irradiated: two sites on the dorsolateral aspect of the neck (left and right), two sites on each hind limb (lateral and medial aspect of the thigh). Dermal dosing formulations are applied to the dermal treatment sites on Day 0 following irradiation. The following applications (Day 1 to 6) were performed on the same time of the day of the first application.

| Day # | Erythema Site 2 | Erythema Site 3 | Erythema Site 4 | Erythema Site 5 | Erythema Site 6 | Edema | Edema Site 2 | Edema Site 3 | Edema Site 4 | Edema Site 5 | Edema Site 6 |
|---|---|---|---|---|---|---|---|---|---|---|---|
| Ctrl | | | | | | | | | | | |
| 1 | 0 | 1 | 0 | 1 | 1 | 0 | 0 | 1 | 0 | 1 | 0 |
| 2 | 0 | 1 | 0 | 1 | 0 | 0 | 0 | 1 | 0 | 1 | 0 |
| 3 | 0 | 1 | 0 | 1 | 1 | 0 | 0 | 1 | 0 | 1 | 0 |
| 4 | 0 | 2 | 0 | 1 | 1 | 0 | 0 | 0 | 0 | 0 | 0 |
| 5 | 1 | 2 | 0 | 2 | 0 | 0 | 0 | 1 | 0 | 1 | 0 |
| 6 | 1 | 2 | 1 | 2 | 1 | 0 | 0 | 1 | 0 | 1 | 0 |
| 8 | 1 | 2 | 1 | 2 | 1 | 0 | 0 | 0 | 0 | 0 | 0 |
| Avg | 0.428571 | 1.571429 | 0.285714 | 1.428571 | 0.714286 | 0 | 0 | 0.714286 | 0 | 0.714286 | 0 |
| BCN512 | | | | | | | | | | | |
| 1 | 0 | 1 | 1 | 2 | 1 | 0 | 0 | 0 | 0 | 1 | 0 |
| 2 | 1 | 1 | 0 | 1 | 1 | 0 | 0 | 1 | 0 | 1 | 0 |
| 3 | 1 | 1 | 0 | 1 | 1 | 0 | 0 | 1 | 0 | 1 | 0 |
| 4 | 0 | 1 | 0 | 1 | 0 | 0 | 0 | 0 | 0 | 0 | 0 |
| 5 | 1 | 2 | 0 | 2 | 1 | 0 | 0 | 1 | 0 | 1 | 0 |
| 6 | 0 | 2 | 0 | 2 | 1 | 0 | 0 | 1 | 0 | 1 | 0 |
| 8 | 0 | 2 | 0 | 2 | 1 | 0 | 0 | 0 | 0 | 1 | 0 |
| Avg | 0.428571 | 1.428571 | 0.142857 | 1.571429 | 0.857143 | 0 | 0 | 0.571429 | 0 | 0.857143 | 0 |
| BCN057 | | | | | | | | | | | |
| 1 | 0 | 1 | 0 | 1 | 1 | 0 | 0 | 1 | 0 | 0 | 0 |
| 2 | 0 | 1 | 0 | 1 | 1 | 0 | 0 | 1 | 0 | 0 | 0 |
| 3 | 1 | 1 | 0 | 1 | 0 | 0 | 0 | 1 | 0 | 1 | 0 |
| 4 | 0 | 1 | 0 | 1 | 0 | 0 | 0 | 0 | 0 | 0 | 0 |
| 5 | 0 | 1 | 0 | 2 | 0 | 0 | 0 | 0 | 0 | 1 | 0 |
| 6 | 0 | 2 | 1 | 2 | 1 | 0 | 0 | 1 | 0 | 1 | 0 |
| 8 | 0 | 2 | 0 | 2 | 0 | 0 | 0 | 0 | 0 | 0 | 0 |
| Avg | 0.142857 | 1.285714 | 0.142857 | 1.428571 | 0.428571 | 0 | 0 | 0.571429 | 0 | 0.428571 | 0 |

TABLE 3

Legend for draize scoring

| | SCORE |
|---|---|
| ERYTHEMA/ESCHAR FORMATION (Maximum Score = 4) | |
| No erythema | 0 |
| Very slight erythema, barely perceptible (edges are not defined) | 1 |
| Well-defined erythema (pale red in color) | 2 |
| Moderate to severe erythema (definite red in color) | 3 |
| Severe erythema (beet or crimson red in color) and/or eschar formation (scab formation) | 4 |
| EDEMA FORMATION (Maximum Score = 4) | |
| No edema | 0 |
| Very slight edema, barely perceptible (edges are not defined) | 1 |
| Slight edema (edges are not definable but the area is slightly raised) | 2 |

TABLE 3-continued

Legend for draize scoring

| | SCORE |
|---|---|
| Moderate edema (area well-defined and raised approximately mm) | 3 |
| Severe edema (raised more than 1 mm and extending beyond the area of exposure) | 4 |

TABLE 4

Study Design (radiation treatment)

| | Radiation Dose Level (Gy) | | | | | |
|---|---|---|---|---|---|---|
| Group | Site 1 | Site 2 | Site 3 | Site 4 | Site 5 | Site 6 | Animals |
| 1 - Control | 25 | | 35 | | 45 | | 1 |
| 2 Group 2 - BCN512 | | | | | | | 1 |
| 3 Group 3 - BCN057 | | | | | | | 1 |

TABLE 5

Study Design (dermal treatment)

| Group | Dose Conc. (mg/mL) | Dose Volume/Site | Animals |
|---|---|---|---|
| 1 Control* | 0 | 0.5 ml | 1 |
| 2 Group 2 - BCN512 | 10 mg/mL | | 1 |
| 3 Group 3 - BCN057 | 10 mg/mL | | 1 |

*Group 1 animal receive the reference item/vehicle, Dimethyl sulfoxide, DMSO in sites 1, 3 and 5 only, sites 2, 4 and 6 sites will not receive the reference item/vehicle.

FIG. 24 shows photographs of the wounds analyzed with Draize scoring. The radiation induced dermatitis study show that the drugs reduce radiation dermatitis. This condition is a dose limiting condition of radiation therapy where the skin is subject to radiation and responds in an inflammatory state presenting erythema and edema. LGR5+ stem cells are present in dermis and are equally affected by radiation. Because of the effects of the drugs on inflammation and stem cell preservation, these drugs protect against radiation dermatitis and support tissue regeneration in the case of injury.

Example 12: BCN057 pH Effect on Formulation

TABLE 6

Figure 22:
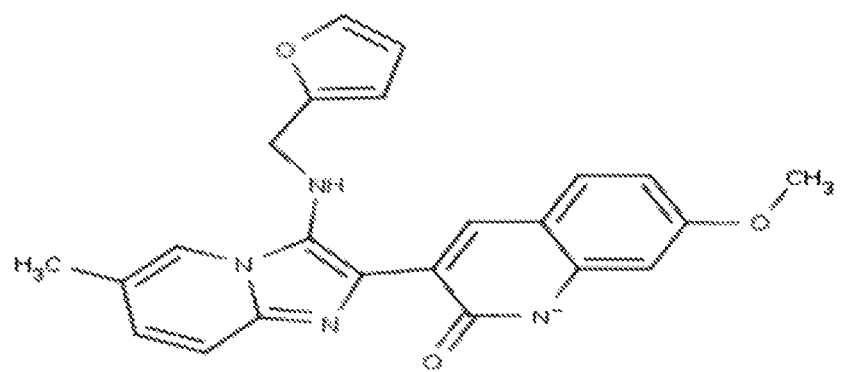
FIG. 22: Species 1-4 for BCN057 formulation experiments.
Figure 23:
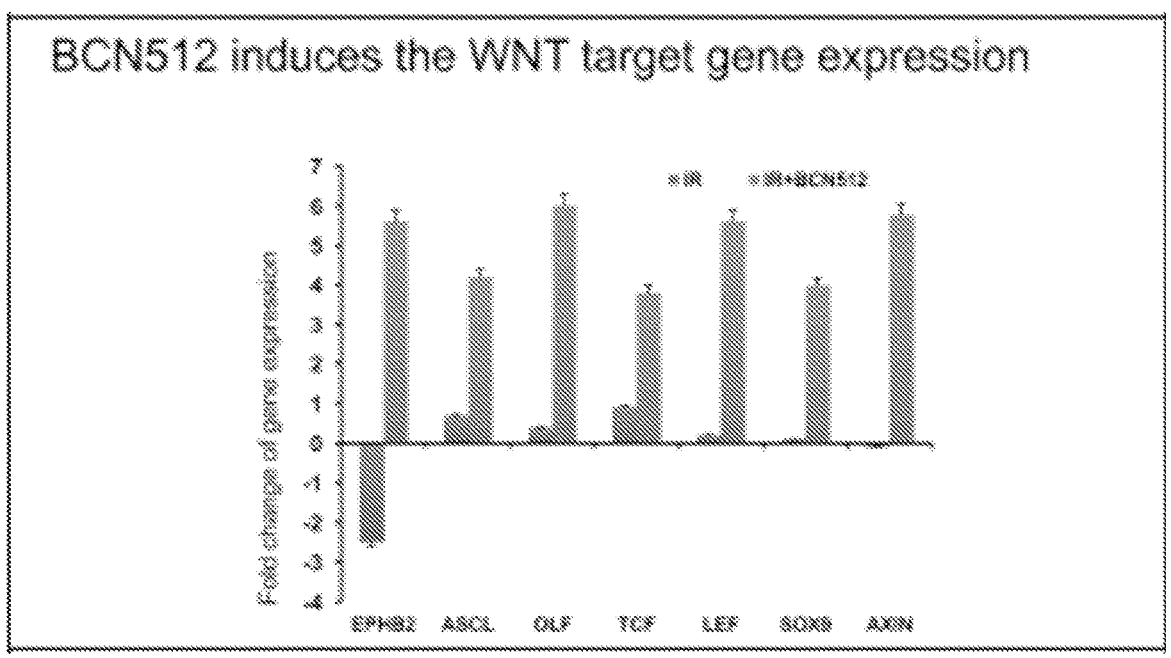
FIG. 23: BCN 512 induces the WINT target gene expression.

BCN057 formulation. Species 1-4 are shown in FIG. 22. The pH of BCN057 is required to be below 5 in order to take a proton and be water soluble. We have successfully used cylodextrins with BCN057 which will work if you drive it into solution at low pH. It will not work if you do not solubilize it first. In conclusion, the reduction in pH below 4.0 provides a soluble version of BCN057 and this gives significant advantage in drug handling and formulation.

| pH | 1% | 2% | 3% | 4% | Species |
|---|---|---|---|---|---|
| 0 | 0 | 99.85 | 0 | 0.1 | |
| 0.2 | 0 | 99.9 | 0 | 0.07 | |
| 0.4 | 0 | 99.94 | 0 | 0.04 | |
| 0.6 | 0 | 99.96 | 0 | 0.03 | |
| 0.8 | 0.01 | 99.97 | 0 | 0.02 | |
| 1 | 0.01 | 99.98 | 0 | 0.01 | |
| 1.2 | 0.01 | 99.98 | 0 | 0.01 | 1 |

TABLE 6-continued

BCN057 formulation. Species 1-4 are shown in FIG. 22. The pH of BCN057 is required to be below 5 in order to take a proton and be water soluble. We have successfully used cylodextrins with BCN057 which will work if you drive it into solution at low pH. It will not work if you do not solubilize it first. In conclusion, the reduction in pH below 4.0 provides a soluble version of BCN057 and this gives significant advantage in drug handling and formulation.

| pH | 1% | 2% | 3% | 4% | Species |
|---|---|---|---|---|---|
| 1.4 | 0.02 | 99.97 | 0 | 0 | |
| 1.6 | 0.04 | 99.96 | 0 | 0 | |
| 1.8 | 0.06 | 99.94 | 0 | 0 | |
| 2 | 0.09 | 99.9 | 0 | 0 | |
| 2.2 | 0.15 | 99.85 | 0 | 0 | |
| 2.4 | 0.23 | 99.76 | 0 | 0 | |
| 2.6 | 0.37 | 99.63 | 0 | 0 | |
| 2.8 | 0.59 | 99.41 | 0 | 0 | 2 |
| 3 | 0.93 | 99.07 | 0 | 0 | |
| 3.2 | 1.46 | 98.54 | 0 | 0 | |
| 3.4 | 2.3 | 97.7 | 0 | 0 | |
| 3.6 | 3.59 | 96.41 | 0 | 0 | |
| 3.8 | 5.58 | 94.42 | 0 | 0 | |
| 4 | 8.56 | 91.44 | 0 | 0 | |
| 4.2 | 12.92 | 87.08 | 0 | 0 | |
| 4.4 | 19.04 | 80.96 | 0 | 0 | 3 |
| 4.6 | 27.16 | 72.84 | 0 | 0 | |
| 4.8 | 37.14 | 62.86 | 0 | 0 | |
| 5 | 48.36 | 51.64 | 0 | 0 | |
| 5.2 | 59.75 | 40.25 | 0 | 0 | |
| 5.4 | 70.17 | 29.83 | 0 | 0 | |
| 5.6 | 78.85 | 21.15 | 0 | 0 | |
| 5.8 | 85.53 | 14.47 | 0 | 0 | |
| 6 | 90.35 | 9.65 | 0 | 0 | 4 |
| 6.2 | 93.69 | 6.31 | 0 | 0 | |
| 6.4 | 95.92 | 4.08 | 0 | 0 | |
| 6.6 | 97.39 | 2.61 | 0 | 0 | |
| 6.8 | 98.34 | 1.66 | 0 | 0 | |
| 7 | 98.94 | 1.06 | 0 | 0 | |
| 7.2 | 99.33 | 0.67 | 0 | 0 | |
| 7.4 | 99.58 | 0.42 | 0 | 0 | |
| 7.6 | 99.73 | 0.27 | 0 | 0 | |
| 7.8 | 99.83 | 0.17 | 0 | 0 | |
| 8 | 99.89 | 0.11 | 0 | 0 | |
| 8.2 | 99.93 | 0.07 | 0 | 0 | |
| 8.4 | 99.95 | 0.04 | 0 | 0 | |
| 8.6 | 99.97 | 0.03 | 0.01 | 0 | |
| 8.8 | 99.97 | 0.02 | 0.01 | 0 | |
| 9 | 99.97 | 0.01 | 0.02 | 0 | |
| 9.2 | 99.97 | 0.01 | 0.03 | 0 | |
| 9.4 | 99.95 | 0 | 0.04 | 0 | |
| 9.6 | 99.93 | 0 | 0.07 | 0 | |
| 9.8 | 99.89 | 0 | 0.11 | 0 | |
| 10 | 99.83 | 0 | 0.17 | 0 | |
| 10.2 | 99.73 | 0 | 0.27 | 0 | |
| 10.4 | 99.58 | 0 | 0.42 | 0 | |
| 10.6 | 99.33 | 0 | 0.67 | 0 | |
| 10.8 | 98.94 | 0 | 1.06 | 0 | |
| 11 | 98.34 | 0 | 1.66 | 0 | |
| 11.2 | 97.39 | 0 | 2.61 | 0 | |
| 11.4 | 95.92 | 0 | 4.08 | 0 | |
| 11.6 | 93.69 | 0 | 6.31 | 0 | |
| 11.8 | 90.35 | 0 | 9.65 | 0 | |
| 12 | 85.53 | 0 | 14.47 | 0 | |
| 12.2 | 78.86 | 0 | 21.14 | 0 | |
| 12.4 | 70.18 | 0 | 29.82 | 0 | |
| 12.6 | 59.75 | 0 | 40.25 | 0 | |
| 12.8 | 48.37 | 0 | 51.63 | 0 | |
| 13 | 37.15 | 0 | 62.85 | 0 | |
| 13.2 | 27.16 | 0 | 72.84 | 0 | |
| 13.4 | 19.05 | 0 | 80.95 | 0 | |
| 13.6 | 12.93 | 0 | 87.07 | 0 | |
| 13.8 | 8.57 | 0 | 91.43 | 0 | |
| 14 | 5.58 | 0 | 94.42 | 0 | |

REFERENCES

1. Monks, A.; Scudiero, D. A.; Skehan, P.; Shoemaker, R. H.; Paull, K. D.; Vistica, D. T.; Hose, C.; Langley, J.; Cronice, P.; Vaigro-Wolf, M.; Gray-Goodrich, M.; Campbell, H.; Mayo, M. R. JNCI, J. Natl. Cancer Inst. 1991, 83, 757-766.
2. Alley, M. C.; Scudiero, D. A.; Monks A.; Hursey, M. L.; Czerwinski, M. J.; Fine, D. L.; Abbott, B. J.; Mayo, A.; Shoemaker, R. H.; Boyd, M. R. Cancer Res. 1988, 48, 589-601.
3. Shoemaker, R. H.; Monks, A.; Alley, M. C.; Scudiero, D. A.; Fine, D. L.; McLemore, T. L.; Abbott, B. J.; Paull, K. D.; Mayo, J. G.; Boyd, M. R. Prog. Clin. Biol. Res. 1988, 276, 265-286.
4. Stinson, S. F.; Alley, M. C.; Kenny, S.; Fiebig, H.; Boyd, M. R. Proc. Am. Assoc. Cancer Res. 1989, 30,613.
5. Rubinstein, L. V.; Shoemaker, R. H.; Paull, K. D.; Simon, R. M.; Tosini, S.; Skehan, P.; Scudiero, D. A.; Monks, A.; Boyd, M. R. JNCI, J. Natl. Cancer Inst. 1990, 82, 1113-1118.
6. Skehan, P.; Storeng, R.; Scudiero, D. A.; Monks, A.; McMahon, J.; Vistica, D. T.; Warren, J. T.; Bokesch, H.; Kenny, F.; Boyd, M. R. JNCI, J. Natl. Cance In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of treating fibrosis in a subject in need thereof, the method comprising administering to the subject a therapeutically effective amount of BCN512 according to the following structure:

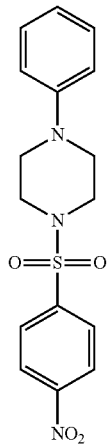

BCN512 wherein the fibrosis is not induced by ionizing radiation.

2. The method of claim 1, wherein the fibrosis is a fibrotic disease selected from the group consisting of idiopathic pulmonary fibrosis, liver fibrosis, gastrointestinal fibrosis and renal fibrosis from kidney dialysis.

3. The method of claim 1, wherein the fibrosis is pulmonary fibrosis, idiopathic pulmonary fibrosis, acute respiratory distress syndrome, cystic fibrosis, non-cystic fibrosis bronchiectasis, cirrhosis, liver fibrosis caused by chronic viral hepatitis B, liver fibrosis caused by chronic viral hepatitis C, endomyocardial fibrosis, old myocardial infarction, atrial fibrosis, mediastinal fibrosis (soft tissue of the mediastinum), myelofibrosis (bone marrow), retroperitoneal fibrosis, progressive massive fibrosis, nephrogenic systemic fibrosis, Crohn's disease, gastrointestinal fibrosis, keloid conditions, scleroderma/systemic sclerosis, arthofibrosis, peyronie's disease, dupuytren's contracture, oral submucous fibrosis, skin fibrosis or adhesive capsulitis.

4. A method of treating fibrosis in a subject in need thereof, comprising administering a therapeutically effective amount of an analog of BCN512 to the subject, wherein the analog is selected from the group consisting of:

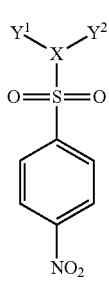

Formula IIB wherein:

$Y^1$ and $Y^2$ taken together with X form:

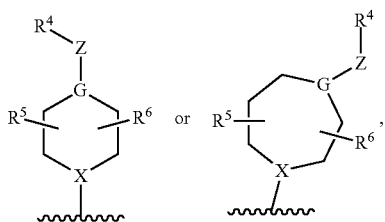

and wherein:

X is N;

G is N;

Z is absent or selected from substituted or unsubstituted alkyl, heteroalkyl, alkenyl, or alkynyl;

$R^4$ is absent or selected from substituted or unsubstituted aryl; and $R^5$ and $R^6$ are each independently absent or lower alkyl wherein the fibrosis is not induced by ionizing radiation.

5. The method of claim 1, wherein the fibrosis is skin fibrosis and results from psoriasis, eczema, dermatitis, scleroderma, ulcers, erosions, trauma, burns, bullous disorders, ischemia of the skin or mucous membranes, ichthyoses, epidermolysis bullosae, hypertrophic scars, keloids, cutaneous changes of intrinsic aging, photoaging, frictional blistering caused by mechanical shearing of the skin and cutaneous atrophy resulting from the topical use of corticosteroids, and/or inflammation of mucous membranes.

6. The method of claim 4, wherein the fibrosis is pulmonary fibrosis, idiopathic pulmonary fibrosis, acute respiratory distress syndrome, cystic fibrosis, non-cystic fibrosis bronchiectasis, cirrhosis, liver fibrosis caused by chronic viral hepatitis B, liver fibrosis caused by chronic viral hepatitis C, endomyocardial fibrosis, old myocardial infarction, atrial fibrosis, mediastinal fibrosis (soft tissue of the mediastinum), myelofibrosis (bone marrow), retroperitoneal fibrosis, progressive massive fibrosis, nephrogenic systemic fibrosis, Crohn's disease, gastrointestinal fibrosis, keloid conditions, scleroderma/systemic sclerosis, arthofibrosis, peyronie's disease, dupuytren's contracture, oral submucous fibrosis or adhesive capsulitis.

7. The method of claim 4, wherein the fibrosis is skin fibrosis and results from psoriasis, eczema, dermatitis, scleroderma, ulcers, erosions, trauma, burns, bullous disorders, ischemia of the skin or mucous membranes, ichthyoses, epidermolysis bullosae, hypertrophic scars, keloids, cutaneous changes of intrinsic aging, photoaging, frictional blistering caused by mechanical shearing of the skin and cutaneous atrophy resulting from the topical use of corticosteroids, and/or inflammation of mucous membranes.

* * * * *